United States Patent [19]
Clay et al.

[11] Patent Number: 5,198,197
[45] Date of Patent: Mar. 30, 1993

[54] APPARATUS AND METHOD FOR SUPERCRITICAL FLUID EXTRACTION

[75] Inventors: Dale L. Clay; Robert W. Allington, both of Lincoln, Nebr.

[73] Assignee: Isco, Inc., Lincoln, Nebr.

[21] Appl. No.: 908,458

[22] Filed: Jul. 6, 1992

Related U.S. Application Data

[60] Division of Ser. No. 795,987, Nov. 22, 1991, which is a continuation-in-part of Ser. No. 553,119, Jul. 13, 1990, Pat. No. 5,094,753.

[51] Int. Cl.$^5$ .............................................. B01D 11/00
[52] U.S. Cl. ........................................ 422/256; 210/634
[58] Field of Search .................. 210/634; 203/16, 19; 422/256–260

[56] References Cited
U.S. PATENT DOCUMENTS 4,770,780 9/1988 Moses .................................. 210/634

Primary Examiner—Frank Sever
Attorney, Agent, or Firm—Vincent L. Carney

[57] ABSTRACT

An apparatus for supercritical fluid extraction incorporates a removable extraction cartridge which in operation has insignificant pressure difference between its inside and outside walls. Because of the low pressure difference, the extraction cartridge need not have the strength to withstand significant pressure and can be made out of molded plastic for disposable use as well as stainless steel and/or machined plastic for reusability. The extraction cartridge can be removed and opened for sample access without the use of tools. The outside of the cartridge can be purged after it is installed in a heated high pressure vessel to remove contamination from its exterior. In one embodiment, the extractor includes a fraction collector for extractments, an automatic sample changer and an automatic carteidge transfer mechanism which provide completely automated extractions.

5 Claims, 16 Drawing Sheets

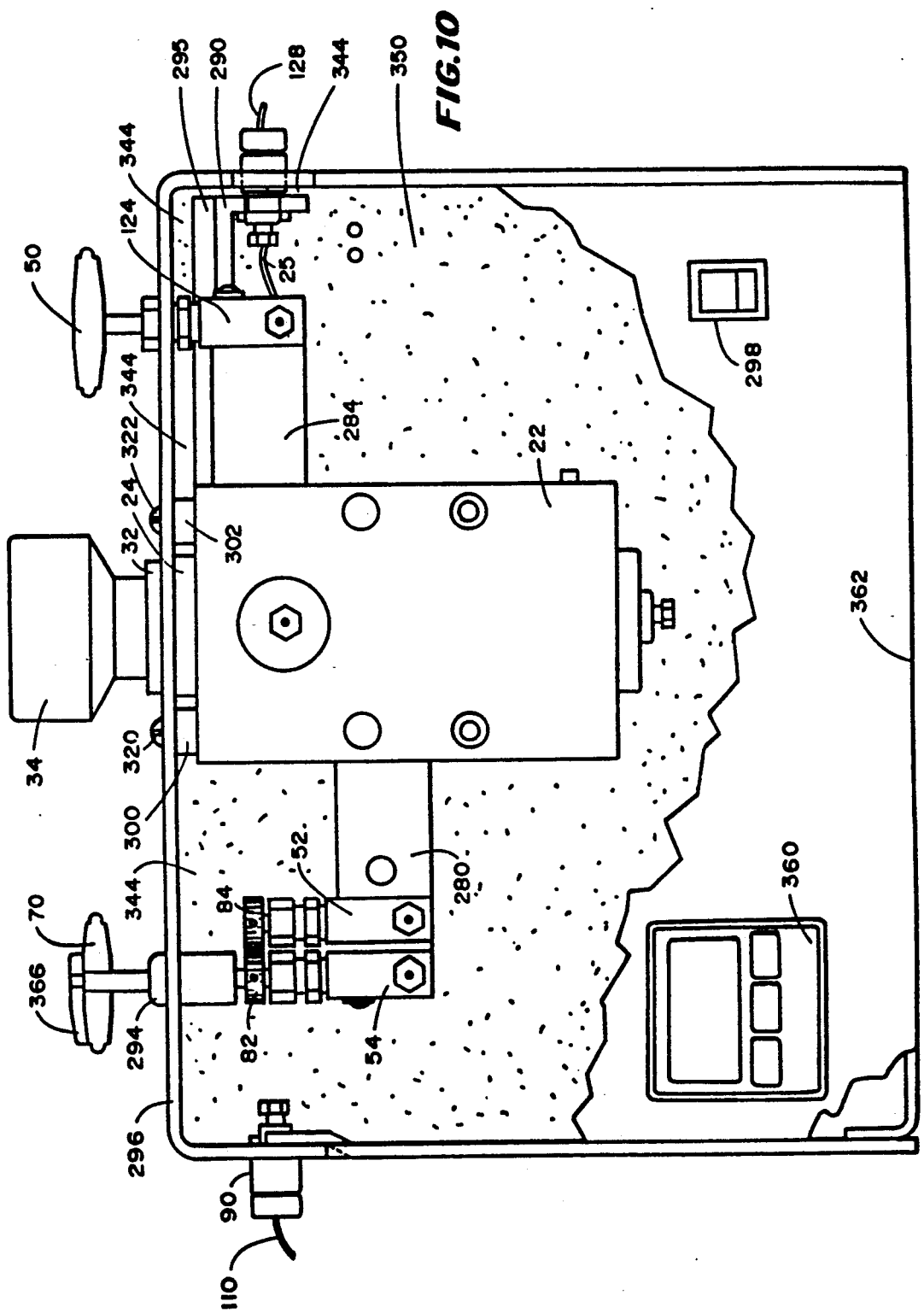

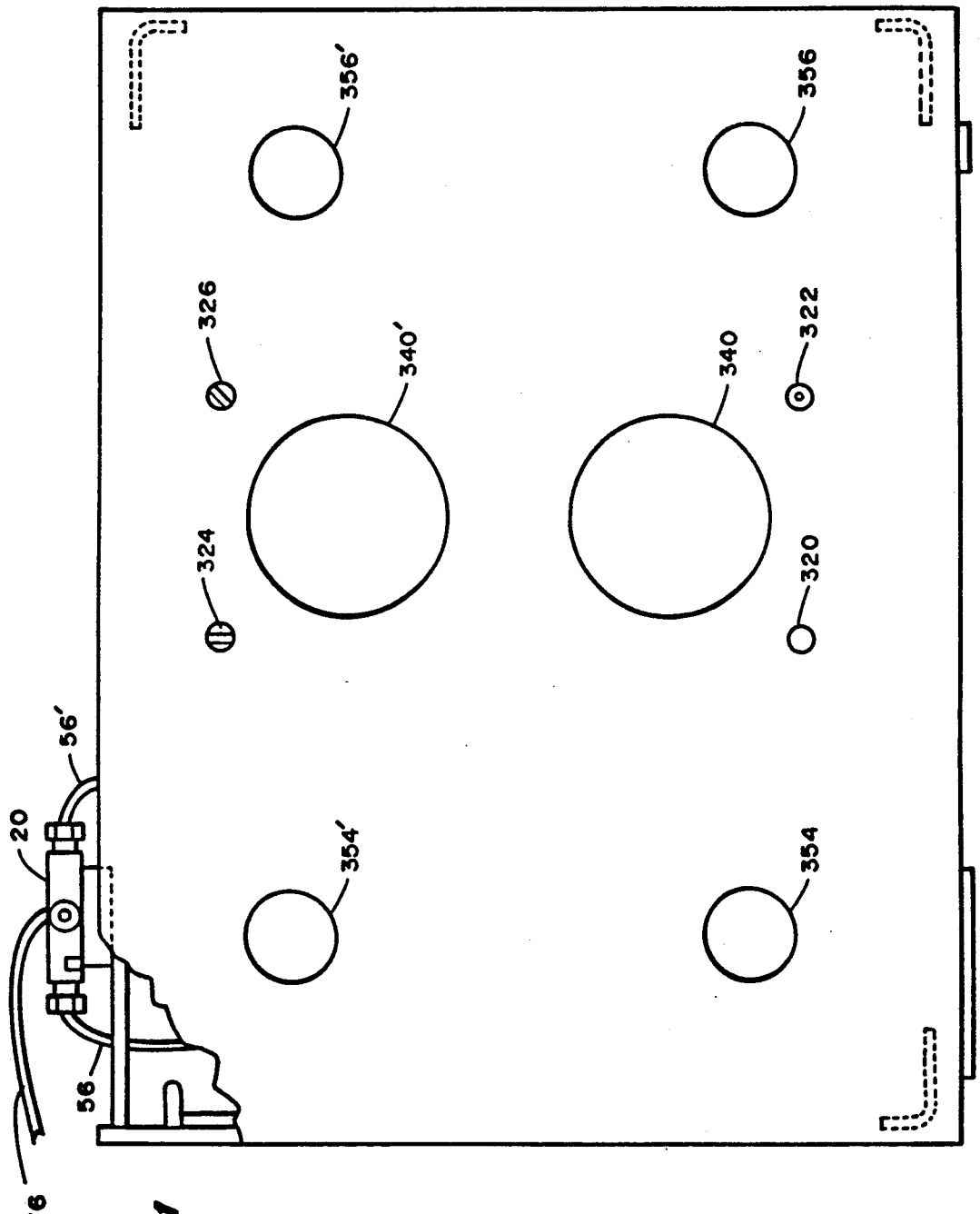

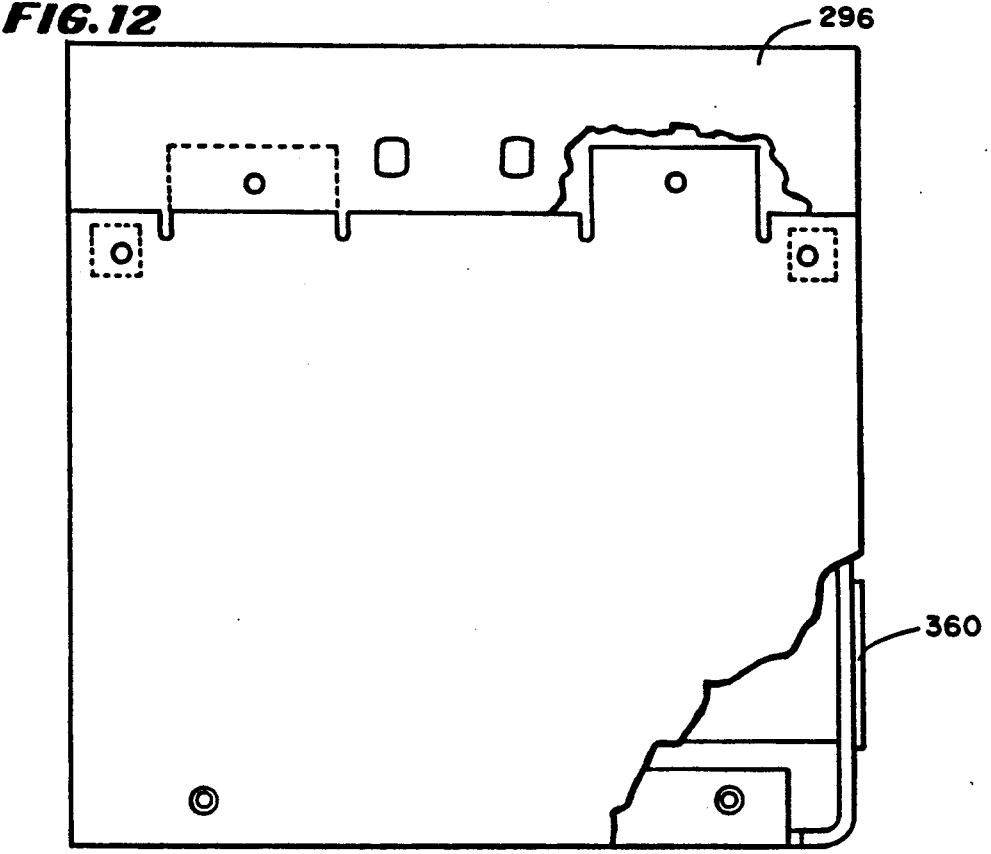
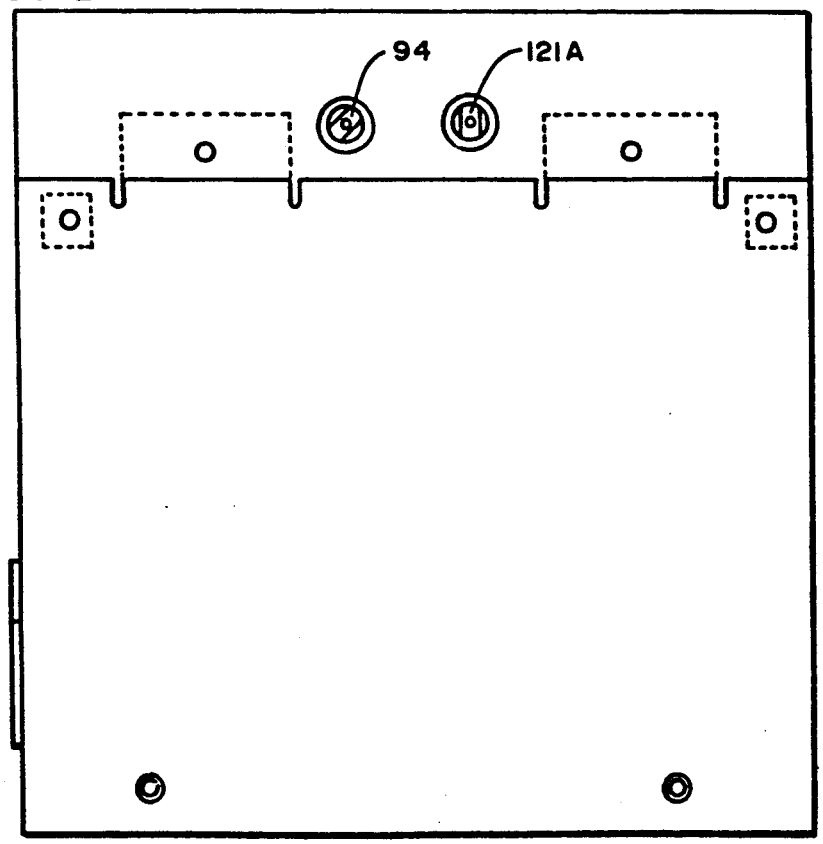

APPARATUS AND METHOD FOR SUPERCRITICAL FLUID EXTRACTION

RELATED CASE

This application is a division of application Ser. No. 07/795,987, filed Nov. 22, 1991, pending which is a continuation-in-part of U.S. patent application Ser. No. 07/553,119, filed July 13, 1990 now, U.S. Pat. No. 5,094,753 for APPARATUS AND METHOD FOR SUPERCRITICAL FLUID EXTRACTION.

BACKGROUND OF THE INVENTION

This invention relates to supercritical fluid extraction.

In supercritical fluid extraction, an extraction vessel is held at a temperature above the critical point and is supplied with fluid at a pressure above the critical pressure. Under these conditions, the fluid within the extraction vessel is a supercritical fluid. In one type of apparatus for supercritical extraction, there is a specially constructed extraction vessel within a source of heat.

A prior art apparatus for supercritical extraction of this type is described by B. W. Wright, et. al., in *ANAL. CHEM.* 59, 38-44 (January 1987) using a glass-lined extraction chamber within a bolted stainless steel extraction vessel heated in an oven. This type of extraction apparatus has the disadvantages of: (1) requiring time consuming steps to open the pressurized extraction vessel before use to insert the sample and again to open it after use to remove the spent sample; and (2) under some circumstances, requiring the handling of a hot extraction vessel.

Prior art apparatuses for automatically changing samples are known. For example, Beckman Instruments, Inc. has produced a radioimmuno and a biogamma analyzer that incorporates a sample changer with an elevator mechanism that raises sample vials from a sample changer to a lead-shielded radiation counting chamber above the sample chamber. Also, a gamma series 300 unit manufactured by Beckman Instruments, Inc., automatically interposes a thick lead shutter that separates the sample vial and the counting chamber from the environment outside the counting chamber. These devices are described in Beckman Bulletin 7250 dated approximately 1972 or 1973. Another apparatus was produced by Micromedic Systems, a division of Rhom and Haas, called the Micromedic Concept 4. It is described in Bulletin M1515 dated 1976.

Two patents describing systems of this type are U.S. Pat. No. 3,257,561 to Packard et al issued June 21, 1966, for RADIOACTIVITY LEVEL DETECTING APPARATUS FOR SAMPLES CARRIED BY PORTABLE TRAYS WITH TRANSFER AND INDEXING MEANS FOR THE TRAYS and U.S. Pat. No. 3,198,948 to Olson issued Aug. 3, 1965, for APPARATUS FOR MEASURING ACTIVITY LEVELS OF RADIOACTIVE SAMPLES.

These devices are not suitable for handling the high temperature, high pressure fluid systems necessary for supercritical extraction.

SUMMARY OF THE INVENTION

Accordingly, it is an object of the invention to provide a novel supercritical extraction technique.

It is a still further object of the invention to provide novel supercritical extraction apparatus.

It is a further object of the invention to provide a supercritical extraction technique which is able to use less expensive containers for samples to be extracted than prior techniques.

It is a further object of the invention to provide a supercritical extraction technique which is faster and more convenient than prior techniques.

It is a still further object of the invention to provide a supercritical extraction apparatus in which the sample to be extracted may be more easily and more quickly inserted into the extraction apparatus and removed therefrom after extraction than heretofor possible.

It is a still further object of the invention to provide a supercritical extraction apparatus and method in which a series of samples may be automatically processed with a minimum of handling by an operator.

In accordance with the above and further objects of the invention, a supercritical fluid extraction system includes a cartridge capable of holding the sample to be extracted and a pressure vessel into which the cartridge fits. The pressure vessel fits into a heater and the cartridge is removably mounted to a breech plug that seals the pressure vessel. There are separate outlets for the cartridge and pressure vessel to permit equalization of pressure on the inside and outside of the cartridge without contamination from impurities outside the cartridge but inside the pressure vessel.

The cartridge: (1) may be removed by a handle that is separated from the cartridge by a thermal barrier and extends outside of the pressure vessel so that the cartridge may be removed by the handle even though the cartridge is still hot; (2) receives the supercritical fluid at a pressure similar to the pressure in the pressure vessel and at substantially the same time so that the cartridge may be made of plastic and need not be excessively strong since its internal pressure is matched by the pressure outside of it; and (3) is easily fastened to a plug for the pressure vessel and the combination is easily inserted into the pressure vessel and removed from it.

A heating block for heating the cartridge is mounted to hang from the cabinet for the apparatus and the valves and tubing used in supercritical fluid extraction are mounted close enough to be heated by it to avoid premature condensation. The pressure vessel is press fit into the heater and the cartridge fits into the pressure vessel with only slight clearance to reduce heat loss and increase speed of operation.

To automate the operation under the control of a microprocessor, a motor operated fraction collector, a motor operated sample source and a motor operated sample injector automatically move samples and collection containers into an extraction station, injects samples into the extraction pressure vessel, performs extraction and collects extractant in different appropriate collection containers in a timed sequence to permit extracting of a series of samples with minimum human handling.

In the preferred embodiment, a movable motor member is aligned with an opening in a sample cartridge reel that moves sample cartridges carrying samples into the extraction station, and with an opening in the extraction pressure vessel. The movable member is dimensioned to be capable of sealing a correspondingly sized opening in the pressure vessel and adapted to move the sample cartridge into the pressure vessel and seal the pressure vessel. Motors are provided to operate the valves to permit the extraction operation on the cartridge. The movable member is removed from the pressure vessel after extraction and returns the sample cartridge back to the sample reel.

In operation, the sample to be extracted is placed within the cartridge and the cartridge inserted into and sealed within a pressure vessel. Upon insertion, one of two outlet fittings communicates with the interior of the cartridge and the other with the interior of the pressure vessel outside the cartridge. An inlet to the pressure vessel communicates with the outlet of a pump which pumps the supercritical fluid through a path that heats it and into the interior of the pressure vessel and extraction cartridge.

To remove any contaminants from outside of the cartridge, the outlet communicates within the inside of the pressure vessel and outside of the cartridge and thus, permits the supercritical fluid to cleanse the outside of the cartridge and the inside walls of the pressure vessel from contaminants as it flows outwardly to a contaminant collector.

For extraction, the cartridge includes an outlet that cooperates with an extractant outlet of the pressure vessel and is connected to the fraction collector so that supercritical fluid flows into the cartridge, out of a fitting that communicates with the interior of the cartridge and into an appropriate collection container.

In the operation of an automatic supercritical fluid extractor, sample cartridges are disposed in the sample changer and are automatically transported to the pressure vessel for extraction by a supercritical fluid. In the preferred embodiment, this transport is first horizontal in a reel of successive sample vials and then vertical through an opening into the pressure vessel. The transport mechanism seals the pressure vessel and is locked in place and motor-driven valves automatically apply extracting fluid first through a purge cycle and then through one or more extracting cycles to extract fluid. A fraction collector, which in the preferred embodiment is a reel holding container, moves the fraction collector containers into position for collection. In the alternative, extractant fluid tubing may be moved from container to container.

As can be understood from the above description, the supercritical extraction technique has several advantages, such as for example: (1) it is more convenient than prior art extractors; (2) it includes a self-cleaning feature; (3) it includes as one of its components a disposable inexpensive cartridge to hold the samples; and (4) it automates the sample injection and fraction collection part of the extraction process as well as automating the extraction itself.

One reason it is convenient to use is because the cartridge containing the spent sample cools down on the sample reel after extraction and does not have to be manually manipulated while hot. Another reason it is convenient to use is that it is easier to open the cartridge and pressure vessel since there are no bolts or the like, and in some embodiments, the cartridge is disposable. This convenience is significant because it reduces the time of extraction materially. Indeed, the most important convenience is the automation of sample handling and fraction collection as well as the extraction process.

It is less expensive than other automated systems because there is pressure equalization within the extractor and the pressure vessel even though it permits purging of the pressure vessel and extraction through separate outlets. A reduction in cost is obtained because plastic cartridges or weaker metal cartridges may be used since the cartridge does not have to withstand a high pressure difference.

DESCRIPTION OF THE DRAWINGS

The above noted and other features of the invention will be better understood from the following detailed description when considered with reference to the accompanying drawings in which:

FIG. 10 is a front elevational, broken-away view of the dual liquid extraction system of FIGS. 5-9 mounted into a metal cabinet with insulation to facilitate in keeping it's critical components at a proper elevated temperature;

FIG. 11 is a plan view, partly broken away of the embodiment of FIG. 10;

FIG. 12 is an elevational left side view partly broken away of the embodiment of FIG. 10;

FIG. 13 is a right side elevational view of the embodiment of FIG. 10;

DETAILED DESCRIPTION

Figure 1:
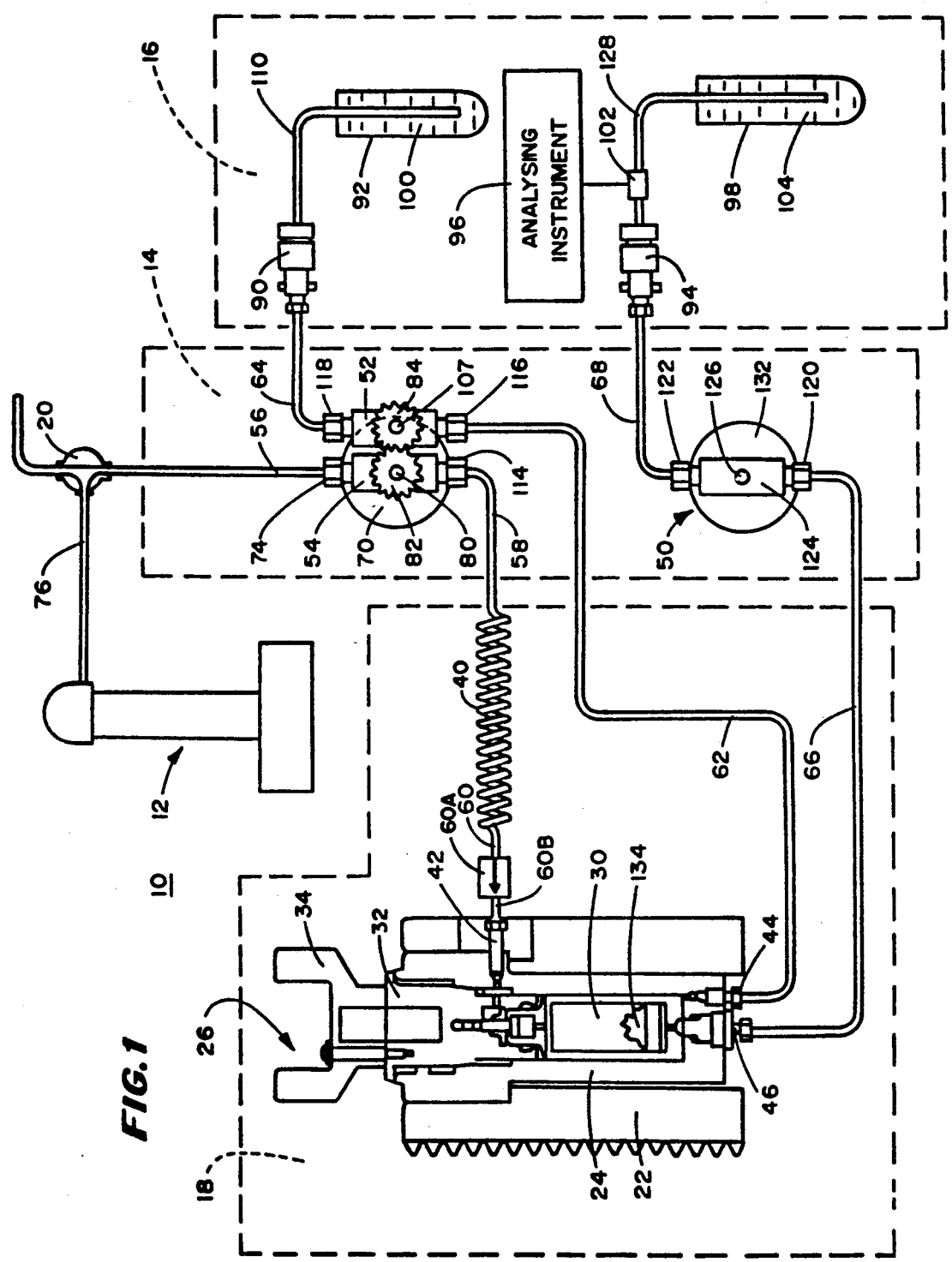
FIG. 1 is a schematic diagram illustrating the operation of a single supercritical fluid extraction system according to the invention.

In FIG. 1, there is shown a schematic fluidic diagram of one channel of a dual-channel supercritical fluid extraction system 10 having a pumping system 12, a valve system 14, a collector system 16 and a pressure vessel and fluid-extraction assembly 18. The pumping system 12 communicates with two extraction cartridges within the pressure vessel and fluid-extraction assembly 18 and for this purpose is connected through a tee joint 20 to two identical valve systems, one of which is shown at 14. Each valve system communicates with a different one of two inlets for the corresponding one of two extraction cartridges.

The pumping system 12 itself is not part of the invention except insofar as it cooperates with the collector system 16, valve system 14 and pressure-vessel and fluid-extraction assembly 18. Any pumping system capable of providing the flow rates and pressures described herein is suitable and one such system is sold by Isco, Inc., P.O. Box 5347, Lincoln, Nebr. 68504, under the designation Isco Model 260D Pump.

The valve system 14 and a second valve system (not shown in FIG. 1) which is connected to the other branch of the tee joint 20 are each connected to two different collector systems 16, one of which is shown in FIG. 1, and to different ones of the two extraction cartridges in the pressure-vessel and fluid-extraction assembly 18 so that, two extraction operations can be performed at the same time using the same pumping system 12. With this arrangement, the valve system 14 causes: (1) supercritical fluid to flow from the pumping system 12 into a space between a cartridge and the interior of the pressure vessel of the pressure-vessel and fluid-extraction assembly 18 for purging the outside of the cartridge and the inside of the pressure vessel; and (2) applies supercritical fluid through the cartridge for extraction of a sample 134 therein. Because the fluid is applied both to the interior of the cartridge and the exterior, the cartridge does not have to withstand a high pressure difference between its interior and exterior and can be made economically.

In addition to controlling the flow of fluid into the pressure-vessel and fluid-extraction assembly 18, the valve system 14 controls the flow of: (1) purging supercritical fluid from the space between the cartridge and interior of the vessel to the collector system 16 or to a vent; and (2) the extractant from the interior of the extraction cartridge to the collector system 16 for separate collection.

To hold sample 134 during an extraction process, the pressure-vessel and fluid-extraction assembly 18 includes a heating block 22, a pressure vessel 24 and a cartridge and plug assembly 26 with the cartridge and plug assembly 26 extending into the pressure vessel 24. The pressure vessel 24 fits within the heating block 22 for easy assembly and disassembly. With this arrangement, the heating block 22 maintains the fluids within the pressure-vessel and fluid-extraction assembly 18 at supercritical fluid temperature and pressure for proper extraction.

The cartridge and plug assembly 26 includes an extraction cartridge assembly 30, a breech plug 32 and a knob 34 which are connected together so that: (1) the pressure vessel 24 is easily sealed with the breech plug 32; (2) the extraction cartridge assembly 30 snaps onto the breech plug 32 and the assembly may be carried by the knob 34; and (3) the knob 34 serves as a handle to insert and fasten the assembly to the tube pressure vessel with the extraction tube communicating with an outlet aligned with its axis and an inlet for the space between the internal walls of the pressure vessel 24 and the exterior of the extraction cartridge 30 and for the interior of the extraction cartridge 30 being provided through a groove circumscribing the assembly inside the pressure vessel 24.

With this arrangement the extraction cartridge assembly 30 may be easily sealed in the pressure vesse 24 by threading the breech plug 32 into it and may be easily removed by unthreading the breech plug 32 and lifting the knob 34. The extraction cartridge assembly 30 contains a hollow interior, an inlet and an outlet so that a sample to be extracted may be placed in the hollow interior and supercritical fluid passed through the inlet, the hollow interior and to the outlet to a collector. The extraction cartridge assembly 30 serves as an extraction chamber or tube, the pressure vessel 24 serves as a extraction vessel and the heating block 22 serves as an oven as these terms are commonly used in the prior art.

In the preferred embodiment, the knob 34 is of a low heat conductivity material and it should include in all embodiments at least a heat insulative thermal barrier located to reduce heating of the handle portion of the knob 34. It extends outside of the pressure vessel 24 and is adapted to aid in the sealing of the pressure vessel 24 and the breech plug 32 together so that the extraction cartridge assembly 30 is within the pressure vessel 24 for maintaining it at the appropriate temperature and the knob 34 is outside the pressure vessel 24 so as to remain cool enough to handle.

Although in the preferred embodiment the knob 34 is a heat insulative material, it only needs to be insulated against heat conducted from the interior of the pressure vessel 24 and this may also be done by a thermal barrier separating the pressure vessel 24 from the knob 34 such as an insulative disc having a width of at least 1 millimeter and extending across the cross-section of the knob 34 to the extent of at least 80 percent of the cross-section to effectively block an considerable amount of transfer of heat between the cartridge and the knob 34. It should have a heat conductivity no greater than 0.05 calories/cm. sec. degree C. at 30 degrees Centigrade.

The extraction cartridge assembly 30 has an opening which permits some supercritical fluid to enter the pressure vessel 24 to follow one path passing into the extraction tube and out through an outlet of the extraction tube into a conduit leading to a collector. Other supercritical fluid follows a second path around the outside of the cartridge to remove contaminants from the pressure vessel 24, equalize pressure and flow from another outlet. One of the inlet and outlet of the extraction cartridge assembly 30 enters along the central axis of the extraction cartridge assembly 30 and the other from the side to permit rotation of parts with respect to each other during seating of the pressure vessel 24 and yet permit communication of the extraction cartridge assembly 30 with the fluid source and with the collector. To reduce wasted heat and fluid, the space between the outside of the cartridge and the inside walls of the pressure vessel 24 is only large enough to accommodate the flow of purging fluid and to equalize pressure between the inside and outside of the cartridge. The volume between the outside of the cartridge and the inside of the pressure vessel 24 is less than 10 cubic centimeters.

In the preferred embodiment, the inlet opens into an annular space between the internal wall of the pressure vessel 24 and the cartridge and plug assembly 26. The fluid follows two paths from the annular space, both of which include an annular manifold with narrow holes and a passageway that communicates with the recess in the breech plug 32. One path opens into the extraction cartridge assembly 30. The other passes along the narrow space outside the extraction cartridge assembly 30. Thus, supercritical fluid enters the extraction tube through a labrythian like path and at the same time passes outside the extraction tube so that the pressure inside the extraction tube is always substantially the same as that inside the pressure vessel 24. Because the pressures are substantially the same, the tube itself may be formed of relatively inexpensive plastics notwithstanding that a high pressure is desirable for extraction from the sample within the extraction tube.

The pressure vessel 24 is generally formed of strong material such as metal and is shaped as a container with an open top, an inlet opening and two outlet openings. The inlet opening is sized to receive an inlet fitting 42, the inlet fitting 42 being shown in FIG. 1 connected in series with check valve 60A to corresponding heat exchanger 40. Each of the two outlet openings are sized to receive a different one of a corresponding purge valve fitting 44, and a corresponding extractant fluid fitting 46. With these fittings, the pressure vessel 24 is able to receive the cartridge and plug assembly 26 in its open end and permit communication between the cartridge and the extractant fluid fittings such as shown at 46. The inlet fittings such as shown at 42 and purge valve fitting, such as 44, permit communication with the inside of the pressure vessel 24.

To control the flow of fluids to and from the pressure vessel and fluid-extraction assembly 18, the valve system 14 includes an extractant valve 50, a purge fluid valve 52 and an extracting fluid valve 54.

To introduce extracting fluid into the pressure-vessel and fluid-extraction assembly 18, the extracting fluid valve 54 communicates with one branch of the tee joint 20 through tube 56 and with one end of the heat exchanger 40 through tube 58, the other end of the heat exchanger 40 communicating with the inlet fitting 42 through tube 60, check valve 60A and tube 60B. With these connections, the extracting fluid valve 54 controls the flow of fluid from the pumping system 12 through the heat exchanger 40 and the pressure vessel 24 through the inlet fitting 42.

To remove purge fluid from the pressure vessel 24, the purge fluid valve 52 communicates at one port with the purge valve fitting 44 through tube 62 and with its other port through tube 64 (not shown in FIG. 1) with the collector system 16 or with a vent (not shown) to remove fluid containing contaminants from the exterior of fluid extraction cartridge assembly 30 and the interior of the pressure vessel 24.

To remove extractant from the extraction cartridge assembly 30, the extractant valve 50 communicates at one of its ports through tube 66 with the extractant fluid fitting 46 and through its other port with the collector system 16 through tube 68 for the collecting of the extracted material, sometimes referred to as analyte or extractant, from the sample within the pressure vessel and fluid-extraction assembly 18.

For convenience, the valves 52 and 54 are mounted to be operated by a single manual control knob 70. To supply fluid to the valve system 14: (1) the tube 56 carries pressurized fluid from the pumping system 12 to tee joint 20; (2) tube 76 is connected to one arm of tee joint 20 to carry pressurized fluid to another liquid extraction system unit not shown on FIG. 1; and (3) the remaining arm of the tee joint 20 is connected through the tube 56 to an inlet fitting 74 of extracting fluid valve 54. The valves 50, 52 and 54 are, in the preferred embodiment, SSi type 02-0120.

The extracting fluid valve 54 has a rotary control shaft 80 that is rotated to open and close its internal port. This shaft is operated by hand control knob 70 and carries spur gear 82 pinned to the control shaft 80. Spur gear 84, which is pinned to control shaft 107 of purge fluid valve 52, meshes with spur gear 82 so that when control knob 70 is rotated clockwise, extracting fluid valve 54 is closed, but since the control shaft 107 of purge fluid valve 52 is geared to turn in the opposite direction, the clockwise rotation of knob 70 opens purge fluid valve 52.

The relative locations of the two gears on the two shafts are such that, in the first (clockwise) position of the knob 70, the extracting fluid valve 54 is shut and the purge fluid valve 52 is open. Turning the control knob 70 counterclockwise 130 degrees from this first position opens extracting fluid valve 54 while allowing purge fluid valve 52 to remain open. Thus, both valves are open when the knob 70 is rotated 130 degrees counterclockwise from the first position. When the knob 70 is rotated 260 degrees counterclockwise from the first position, extraction fluid valve 54 is open and purge fluid valve 52 is shut. Thus, there are three definable positions for control knob 70: (1) clockwise with valve 54 shut and valve 52 open; (2) mid position with both valves open; and (3) full counterclockwise with valve 54 open and valve 52 shut.

The extractant valve 50 includes an inlet fitting 120, outlet fitting 122, manual control knob 132 and control shaft 126. The rotary control shaft 126 is attached to control knob 132. When the extractant valve 50 is opened by turning the control knob 132 counterclockwise from its closed position, fluid flows from the extraction cartridge assembly 30, through the extractant fluid fitting 46, the conduit 66, the valve inlet fitting 120, the outlet fitting 122, through the tube 68 and into the collector system 16.

The collector system 16 includes a purge coupling 90, a purge fluid collector 92, an extractant coupling 94, an analyzing instrument 96, and an extractant fluid collector 98. The purge fluid flowing through the valve 52, flows through purge coupling 90 into the capillary tube 110 and from there into the purge fluid collector 92 where it flows into a solvent 100. Similarly, the extractant flowing through valve 50 flows through tube 68 to the extractant coupling 94 and from there to the capillary tube 128 and extractant fluid collector 98 which contains an appropriate solvent 104 in the preferred embodiment.

The analysing instrument 96 may be coupled to the capillary tube 128 through an optical coupling 102 in a manner known in the art. The optical coupling 102 is a photodetector and light source on opposite sides of a portion of the capillary tube 128, which portion has been modified to pass light. This instrument 96 monitors extractant and may provide an indication of its passing into the extractant fluid collector 98 and information about its light absorbance. Other analytical instruments may also be used to identify or indicate other characteristics of the extractant.

Figure 2:
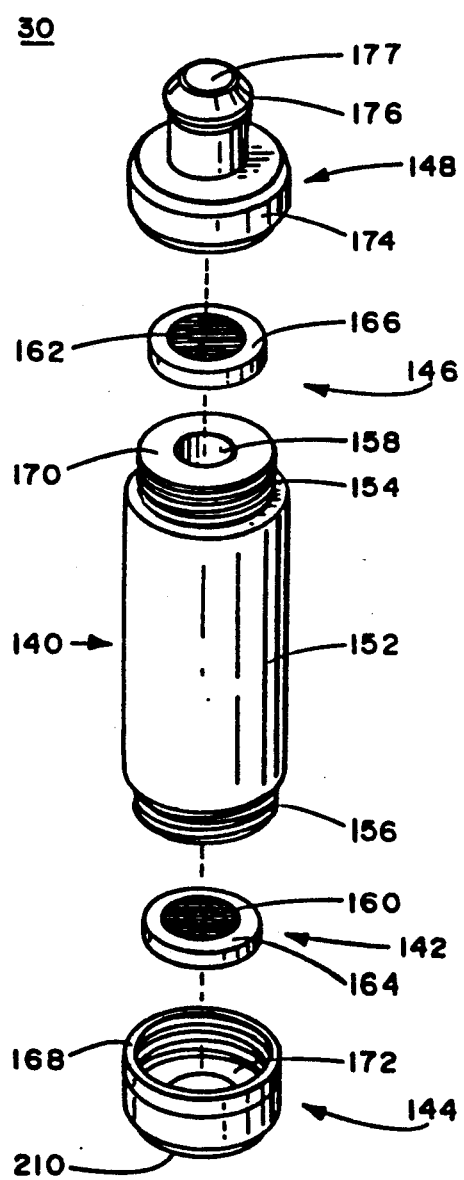
FIG. 2 is an exploded perspective view of an extraction cartridge used in the embodiment of FIG. 1 according to the invention.

In FIG. 2, there is shown an exploded perspective view of the supercritical fluid extraction cartridge assembly 30, having a substantially cylindrical tubular body portion 140, a bottom porous means 142 such as a filter, frit or other means for confining sample, a bottom cap 144, and a top porous means 146 such as a filter, frit, or means for confining sample and a top cap 148.

In one embodiment, the tubular body portion 140 is a cylindrical plastic tube adapted to hold within it the sample 134 (FIG. 1) having shoulders on each end with reduced diameter externally threaded top and bottom end portions 154 and 156. A central opening 158 passes along its axis for receiving sample. However, the tube may take other shapes and be formed of other suitable materials.

To confine the sample, the bottom and top porous means 142 and 146 each include stainless steel porous frit members 160 and 162 held within different ones of two sealing rings 164 and 166 respectively. The frit members 160 and 162 have the same diameter and are arranged to be aligned with the central opening 158 and the sealing rings 164 and 166 have the same internal and external diameter as the end portions 154 and 156 of the tube 152 to lie flat over the tubular body portion 140 with the frit members 160 and 162 closing their ends.

The sealing rings 164 and 166 are preferrably made of Teflon or Kel-F (trademarks of E.I. DuPont de Nemours Co., Wilmington, Del., United States of America for tetrafluoroethylene and other fluorocarbon plastics). The top and bottom caps 144 and 148 include internal threads such as the threads 168 in the bottom cap 144 that engage with corresponding external threaded end portions 156 and 154 of the tube 152 to hold the top and bottom caps 148 and 144 in place.

The bottom cap 144 is sized so that when threaded against the shoulder of the body portion 140, it sealingly forces the ring 164 against the bottom face of the tubular body portion 140 to form a seal and hold the frit member 160 in place. Similarly, the top cap 148 is sized to compress the ring 166 against an annular face 170 of the top end portion 154 of the tubular body portion 140 to form a seal. The bottom cap 144 has an inwardly turned annular flange 175 for engaging the ring 164 with a conical central opening 210 (FIG. 4) for an outlet fitting and a similar flange is in the top cap 148. Within the flanges are corresponding circular apperatures substantially the same size as the porous means 142 and 146 and of the central opening 158 and aligned therewith for the passage of fluid.

The upper cap 148 includes lateral sides 174 having internal threads for compressing the frit member 162 in place and an engaging nipple 176 having an open end 177. The extraction tube 152 may be machined of 303 stainless steel for a permanent cartridge or molded of polyphenylene sulfide, polyetherimide or polyethersulfone plastic for a disposable cartridge. This cartridge has an internal volume for sample of 2.5 cubic centimeters in the preferred embodiment, but may be as large as 1000 cubic centimeters. The top and bottom caps 148 and 144 may be machined from polyetherketone plastic for a permanent cartridge or molded of polyetherimide or polyphenylene sulfide ("Fortron," Celanese Chemical Co., 1211 Avenue of Americas, New York, N.Y. 10036) plastic for a disposable cartridge. If the cartridge is intended for use at temperatures greater than 100 degrees C. it is advantageous to make the caps 144 and 148 and the tubular body 140 from stainless steel.

Figure 3:
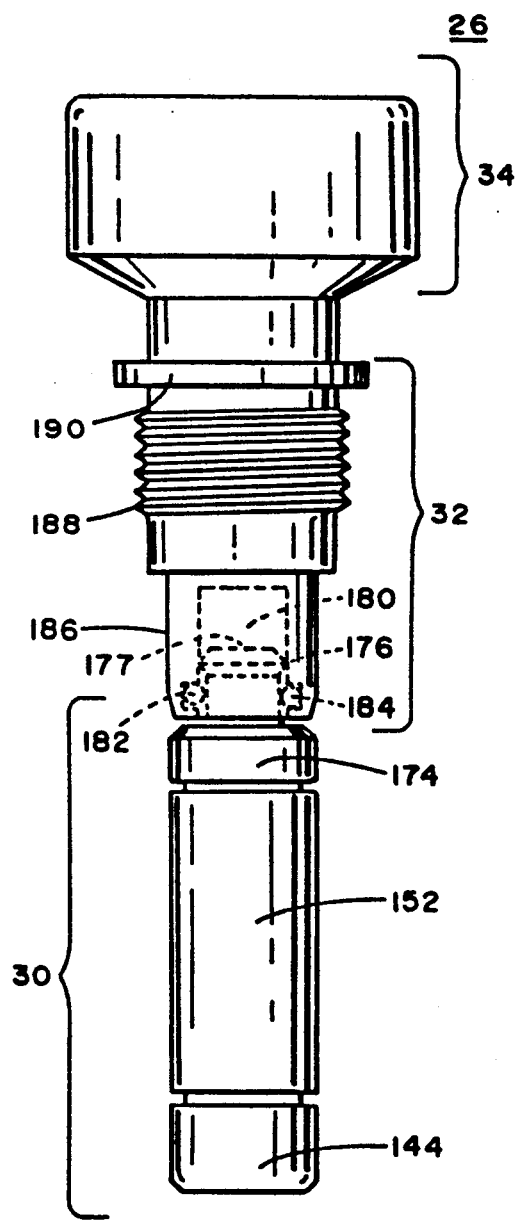
FIG. 3 is an elevational view of the extraction cartridge of FIG. 2 clipped into a breech plug used in the embodiment of FIG. 1.

In FIG. 3, there is shown an assembled cartridge and plug assembly 26 having a breech plug 32, an extraction cartridge assembly 30 and a knob 34.

The breech plug 32 is made of high strength, corrosion resistant, stainless steel (Nitronic 50) and includes cylindrical recess 180, sealing surface 186, engaging thread 188 and annular stop flange 190. The cylindrical recess 180 is positioned to receive engaging nipple 176 on one side and the knob 34 on the other with the external threads 188 between them for forming a closure with the pressure vessel. Near the outer end of the recess 180 is located a retaining groove 182. Within this groove 182 is located a garter spring 184.

The garter spring 184 is a helical coil of stainless steel wire bent into the shape of a circle and welded closed at the ends to form a torus. The turns of the helix are inclined to the helix axis so that they deflect rather than buckle when a circular member of outside diameter greater than the inside diameter of the torus is pressed through the center of the torus while the outside diameter of the torus is constrained by means such as the groove 182. Therefore, upon pressing the extraction cartridge assembly 30 into the recess 180 so that the major diameter of its engaging nipple 176 pops past the garter spring 184, the extraction cartridge assembly 30 is retained in breech plug 32. The strength of retention depends upon the strength of the garter spring 184. The garter spring 184 is chosen so that the cartridge is retained against gravity and other relatively light forces but still is easy to remove manually by pulling it from the breech plug 32.

The knob 34 is fastened to the top of breech plug 32 by any conventional means. In the preferred embodiment, knob 34 is fabricated of temperature-resistant insulating material, such as phenolic plastic and fastened in place.

Figure 4:
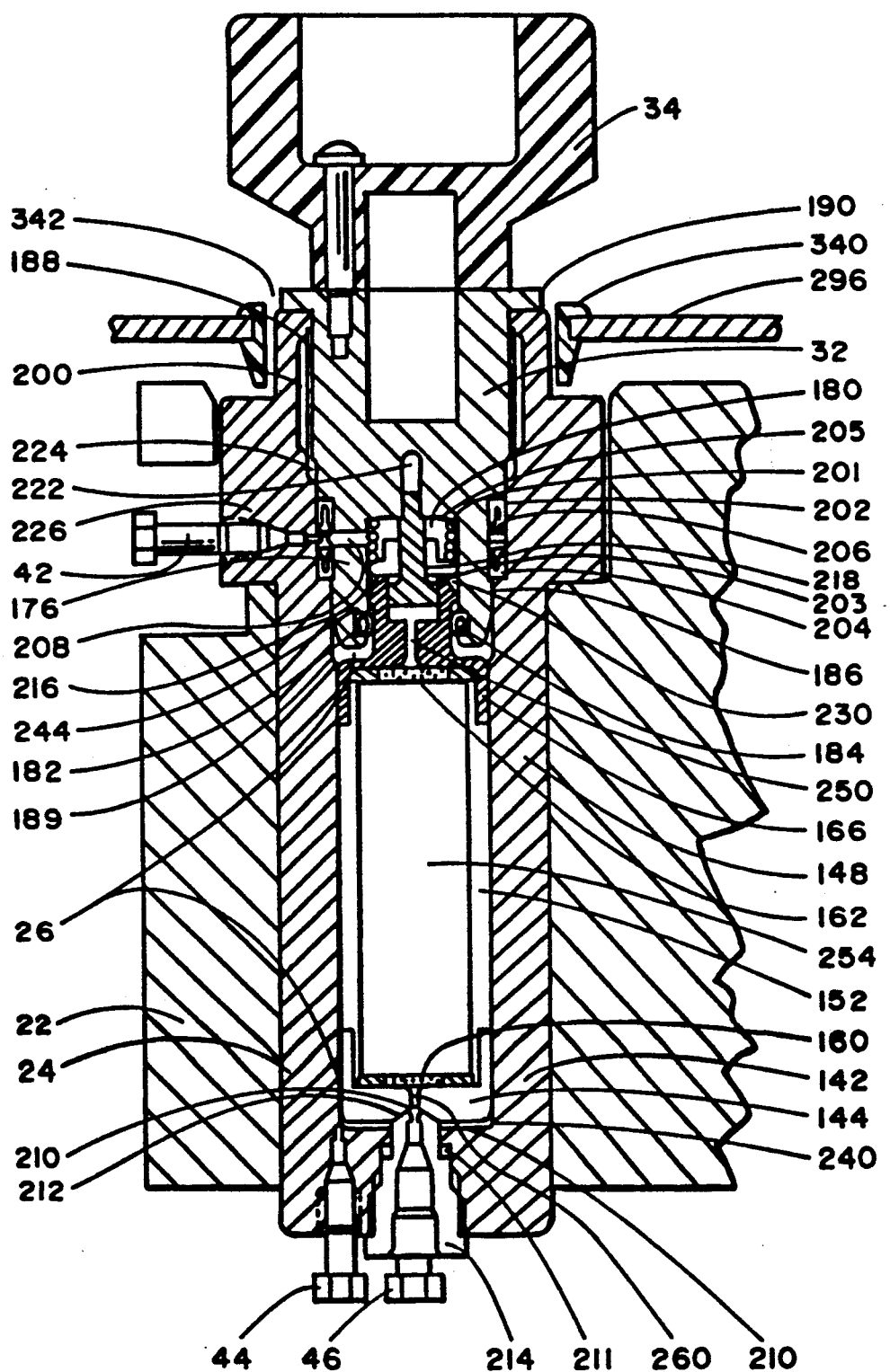
FIG. 4 is a fragmentary sectional view of the extraction cartridge, breech plug pressure vessel and heating block.

In FIG. 4, there is shown a sectional view of the clipped-together extraction cartridge 26, knob 34 and breech plug 32 replaceably installed in pressure vessel 24 which in turn has previously been permanently force fit into heating block 22. The pressure vessel 24 is fabricated of type 303 stainless steel for good machinability and corrosion resistance and has within it a cylindrical central opening sized to receive the extraction cartridge 26, two openings for outlet fittings in its bottom end, an opening in its cylindrical side wall to receive an inlet fitting and an open top with internal threads sized to engage the external threads 188 of the breech plug 32. The heating block 22 is fabricated from aluminum for good thermal conductivity and includes a cylindrical opening sized to tightly receive the pressure vessel 24. The breech plug 32 and the extraction cartridge assembly 30 are a slip fit within the pressure vessel 24. External threads 188 on breech plug 32 engage in internal threads 200 within pressure vessel 24.

An annular self-acting high pressure seal 202 cooperates with a sealing surface 186 to seal high pressure supercritical fluid from the atmosphere and an annular low pressure seal 204 spaced from the annular high pressure seal 202 prevents contaminated supercritical fluid in the space between the interior of the pressure vessel 24 and the exterior of the extraction cartridge assembly 30 from getting back to the supercritical fluid supply. These two annular seals 202 and 204 form between them a torroidal inlet chamber into which the outlet of the fluid inlet 42 extends to introduce fluid. Contamination may arise from fingerprints or other foreign material on the outside wall of extraction cartridge assembly 30 and the low pressure seal 204 protects against this contamination. Seals 202 and 204 are Bal-Seal type 504MB-118-GFP.

Supercritical fluid is supplied to fluid inlet 42 and circulates in the annular space between high pressure seal 202 and low pressure seal 204, and then follows two paths into the pressure vessel 24 and extraction cartridge 30: one path for purging and one path for extraction. An annular spacer 206 within the torroidal opening between seals 202 and 204 has an hour-glass shaped cross section with radial holes through it and distributes incoming supercritical fluid from the inlet of fitting 42 to the opposite side of the spacer 206 from which it flows to passageway 208 drilled in breech plug 32.

Because the passageway 208 extends radially from the recess 180 in the breech plug 32 to the annular ring, it provides an open path for fluid between the two regardless of the orientation of passageway 208. The passageway 208 opens at an uncontrolled angular location with respect to the inlet fixture 42 (inner side). Fluid flows from one side of the inwardly curved portion of the hour glass shaped spacer 206 that communicates with the outlet of fitting 42 to the other side of the inwardly curved portion and from there to the passageway 208.

When the cartridge and plug assembly 26 shown in FIG. 3 are inserted into the pressure vessel 24 as shown in FIG. 4, the knob 34 is rotated and the external threads 188 of the breech plug 32 which form an eight thread per inch connector engage internal threads 200 in the pressure vessel 24, screwing the breech plug 32 and attached cartridge and plug assembly 26 down into the pressure vessel 24. When conical recess 210 in the bottom cap 144 reaches the external conical tip 212 of fitting adapter 214, the cartridge and plug assembly 26 is prevented from moving further down.

Screwing the breech plug 32 in further after the cartridge and plug assembly 26 has bottomed causes the upper flat annular surface of fitting nipple 176 to bear upon the flat lower surface of a hat-shaped washer 216 At this time, the hat-shaped washer 216 is residing against the upper surface of the head of a shoulder screw 218 which is threaded into cylindrical hole 222 in breech plug 32.

Further screwing of the breech plug 32 into the pressure vessel 24 causes the nipple 176 to lift the washer 216 off of the screw head and compress a coil spring 201 between annular surface 205 and the ridge of the washer 216. Continued screwing of the breech plug 32 into the pressure vessel 24 causes annular flange 190 of breech plug 32 to bear upon the upper surface of the pressure vessel 24. This provides a limit stop with the coil spring 201 compressed, as shown in FIG. 4.

The force of the compression spring 201 is enough to provide a low pressure seal between the hat-shaped washer 216 and the upper annular surface 203 of the fitting nipple 176. More importantly, this force also provides a low pressure seal on the mating concical surfaces of the recess 210 of lower cap 144 and the external conical tip 212 of the fitting adapter 214.

The sealing surface 186 acts as a pilot during the initial part of insertion to insure that the internal threads 188 do not get cross-threaded. A taper 189 at the end of the cylindrical sealing surface 186 pilots the breech plug 32 past seals 202 and 204 so that they are not damaged during insertion of the breech plug 32.

The locations of recess 224, passageway 208, high pressure seal 202 and the engaging threads 188 and 200 are chosen such that if the breech plug 32 is inadvertently removed when the interior of the pressure vessel 24 is pressurized, fluid within the pressure vessel 24 leaks past high pressure seal 202 and runs up the flights of the engaging screw threads 188 and 200, and depressurizes the system while there is still adequate screw engagement to ensure safety at the maximum rated operating pressure. The maximum rated operating pressure of the embodiment shown in FIG. 4 is 10,000 psi. The maximum operating temperature is 150 degrees Centigrade. The equipment need not be designed for operating temperatures above 300 degrees Centigrade and pressure above 30,000 pounds per square inch.

After the breech plug 32 and the cartridge and plug assembly 26 are assembled into the pressure vessel 24 as described above, but before an extraction, the space between the cartridge and plug assembly 26 and the pressure vessel 24 is purged of contaminants. During such a purge or cleaning cycle supercritical fluid enters fluid inlet 42, is distributed by the annular spacer 206 and goes through passageway 208. It passes between the outer diameter of hat-shaped washer 216 and the inside cylindrical diameter 230 of the recess within breech plug 32. Fluid then continues down and passes the annular space between the outside diameter of engaging nipple 176 and inside diameter 230 of the recess 180 in breech plug 32. The fluid passes garter spring 184 and circulates with even circumferential distribution around the outside of top cap 148, the extraction tube 152, and the bottom cap 144. The flow is collected in the annular space below the bottom cap 144 and above the bottom 240 of pressure vessel 24 and exits through vent discharge fitting 44, carrying contaminants with it.

Contaminated fluid between the exterior of extraction cartridge 26 and the interior of high pressure vessel 24 does not make its way into the interior of the extraction vessel. Low pressure seal 204 prevents contaminated fluid from reaching passageway 208. A labyrinth seal consisting of the narrow gaps between the major diameter of fitting nipple 176 and the inside diameter 230 of recess 180, and between inside diameter 230 and the outside diameter of the hat-shaped washer 216, prevents contaminants from reaching the space above the hat-shaped washer 216 by diffusion.

During a purge or cleaning cycle, there is downward flow of supercritical fluid through these gaps, and since the gaps are small, this downward fluid flow prevents eddies of contaminated fluid from passing up through the gaps. These gaps are only a few thousandths of an inch. Because the top of nipple 176 and the conical recess 210 at the bottom of the extraction cartridge are sealed by spring pressure, contamination cannot enter in these ways.

For extraction, supercritical fluid entering fitting 42 is distributed in the space occupied by spacer ring 206, flows through passageway 208 and flows down the few thousandths of an inch radial gap between the shoulder of shoulder screw 218 and the inside diameter of washer 216. The fluid continues to flow down and flows through passageway 250, porous frit 162 and into extraction volume 254 where it passes through material to be extracted. Extraction volume 254 is shown sized in FIG. 4 for a 10 cubic centimeter volume to receive sample. After passing the extraction volume fluid, it is exhausted for sample collection through frit 160, passageway 260, fitting adapter 214 and out through fitting 46.

All tubing, except tubing designated as capillary tubing, in this disclosure is 300 series stainless steel with an outside diameter of 1/16 inch and inside diameter 0.02 inch.

In operation after assembly, the fluid flow associated directly with the pure fluid valve 54 (FIG. 1) exiting its port 114 (FIG. 1) flows through tube 58 through the heat exchanger 40, which is formed by coiling a contiguous segment of tubing into a helix, through the check valve 60A and through the tube 60B to the inlet fitting 42 of pressure vessel 24. The heat exchanger 40 actually resides in a longitudinal bore through heating block 22 so that the heat exchanger is at the same temperature as pressure vessel 24 and extraction tube 30. This preheats any fluid flowing into inlet fitting 42 to essentially the same temperature as the extraction cartridge assembly 30. This temperature is above the critical temperature for the fluid. Assuming that the pump 12 is set to produce a constant fluid pressure greater than the critical pressure, fluid entering the pressure vessel 24 will be a supercritical fluid.

The check valve 60A prevents backflow of supercritical fluid out of the pressure vessel 24 and extraction cartridge 26 of a first channel of a dual channel supercritical extraction system if there is a momentary drop in pressure of the supercritical fluid at the location of the tee 20. Such a pressure fluctuation could occur if the second channel of a dual channel extraction system is suddenly purged while the first channel is extracting. Each channel requires such a check valve.

During a purge cycle, contaminated supercritical fluid leaves fitting 44, flows through a tube 62 and enters the inlet fitting 116 of the purge fluid valve 52. Then it exits the outlet fitting 118 and passes through the tube 64 to the coupling 90 (FIG. 1). The coupling 90 couples the quartz capillary tube 110 so that contaminated purge gas exits through it. The bore of the capillary tube is small enough, such as 75 micrometers, and its length long enough, on the order of a few inches, to provide enough fluid resistance to limit the flow to a convenient rate: for example 5 milliliters per minute with respect to displacement of pump 12, at a pressure of 3,000 psi. Pump 12 is a constant pressure pump so this fluid flow does not affect the pressure within pressure vessel 24 once the flow stabilizes.

The outer end of capillary 110 may be immersed a purge fluid collector 92 (FIG. 1) containing an appropriate solvent 100 such as isopropyl alcohol to serve as a collector. Bubbles through this solvent indicate proper flow and the solvent tends to prevent the end of the capillary tube 110 from being plugged by the exhausted contaminants. A solvent is chosen in a manner known in the art to dissolve contaminants so the end of the capillary tube 110 does not plug and so the solvent may later be analyzed if desired to determine whether there was any contaminants on the exterior of the extraction cartridge.

During an extraction cycle, extractant exits fitting 46 on pressure vessel 24 and passes through tube 66. This tubing extends to inlet fitting 120 of extractant valve 50 which has rotary control shaft 126 attached to control knob 132. When the extractant valve 50 is opened by turning it counterclockwise from its closed position, fluid exits from its fitting 122, through tube 68 to fitting 94. Fitting 94 couples to quartz capillary tube 128.

Capillary tube 128 has a small enough bore, such as 50 micrometers, and a long enough length, on the order of several inches, to produce a flow rate, relative to the displacement of constant pressure pump 12, of a conveninent amount. For example, this may be two milliliters per minute. The end of the capillary tube 128 dips into solvent 104 in the extractant collector 98.

Isopropyl alcohol is under some circumstances used for solvent 104. This solvent 104 must be a good solvent for the extractant since it must trap the extractant by dissolving it from the gas bubbling through it and must prevent plugging at the end of the capillary tube 128.

The solvent 104 is removed after extraction and is analyzed to determine the composition and amount of the extractant Because of the pressure and temperature drop along the length of capillary 128 (and also capillary-110) fluid entering the capillary as a supercritical fluid (or a liquid if fitting 90 or fitting 94 is not heated) changes to a gas by the time it reaches the far end where it dips into the solvent which is at room temperature.

In FIGS. 5–9, there are shown, in five orthographic views, the physical structure of a preferred embodiment of an extraction system 10 dual station supercritical extraction apparatus 10. For simplicity, one station of the dual apparatus is shown with its complete fluid connections and only this one is described in detail. The second extraction station is substantially identical to the first. The fluidic connections in FIGS. 5–9 correspond to the connections in FIG. 1. The components described and numbered in FIG. 1 carry like identifying numbers in FIGS. 5–9. A corresponding second extraction station components in FIG. 5 carry corresponding numbers modified with the addition of a prime (') sign.

Figure 5:
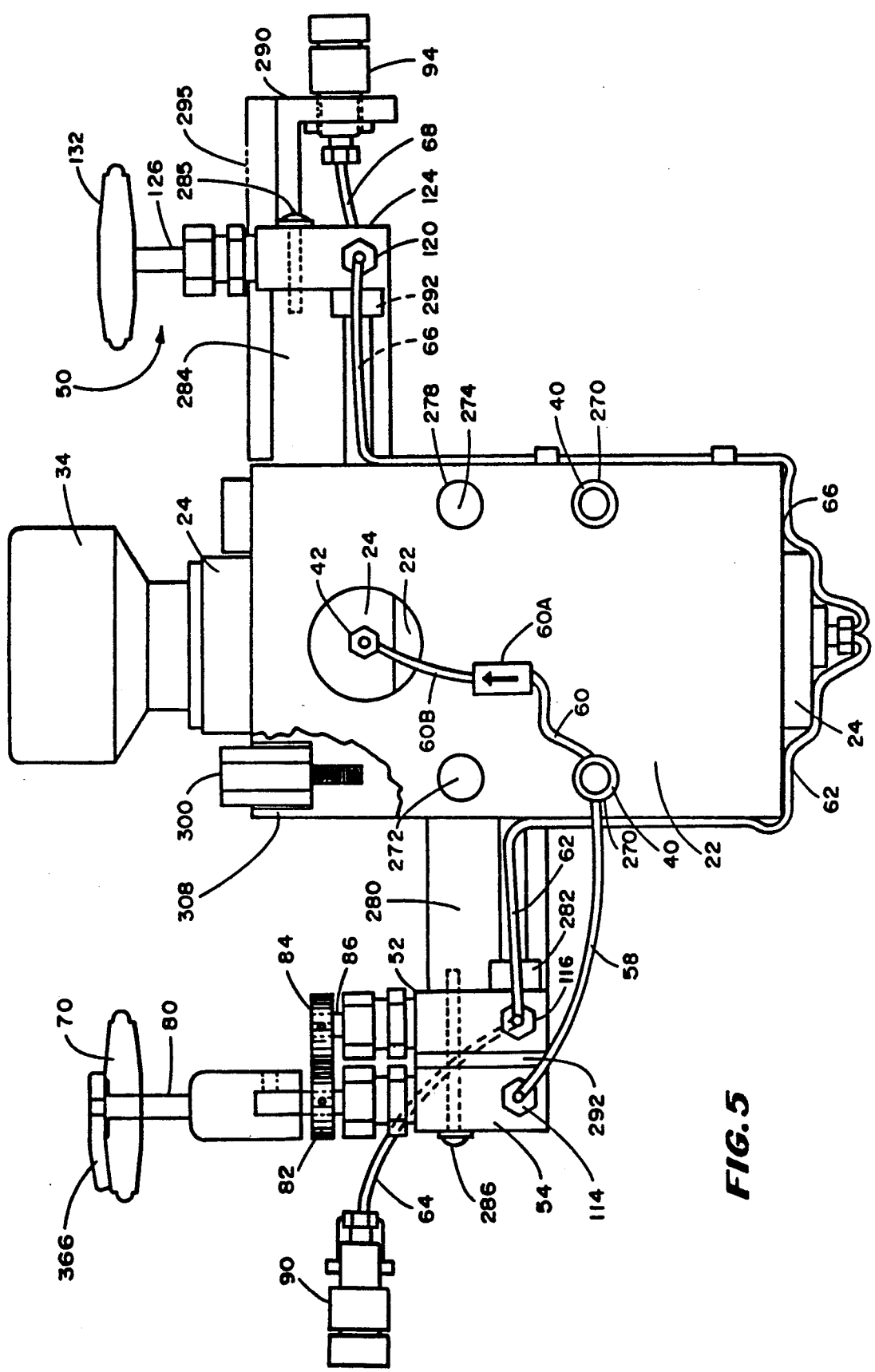
FIGS. 5-8 are four-view orthographic projections showing the major working parts of a dual supercritical fluid liquid extraction system of FIGS. 1-4, with FIG. 5 being a front elevational view, FIG. 6 being a top view, FIG. 7 being a left side elevational view, and FIG. 8 being a right side elevational view.
Figure 6:
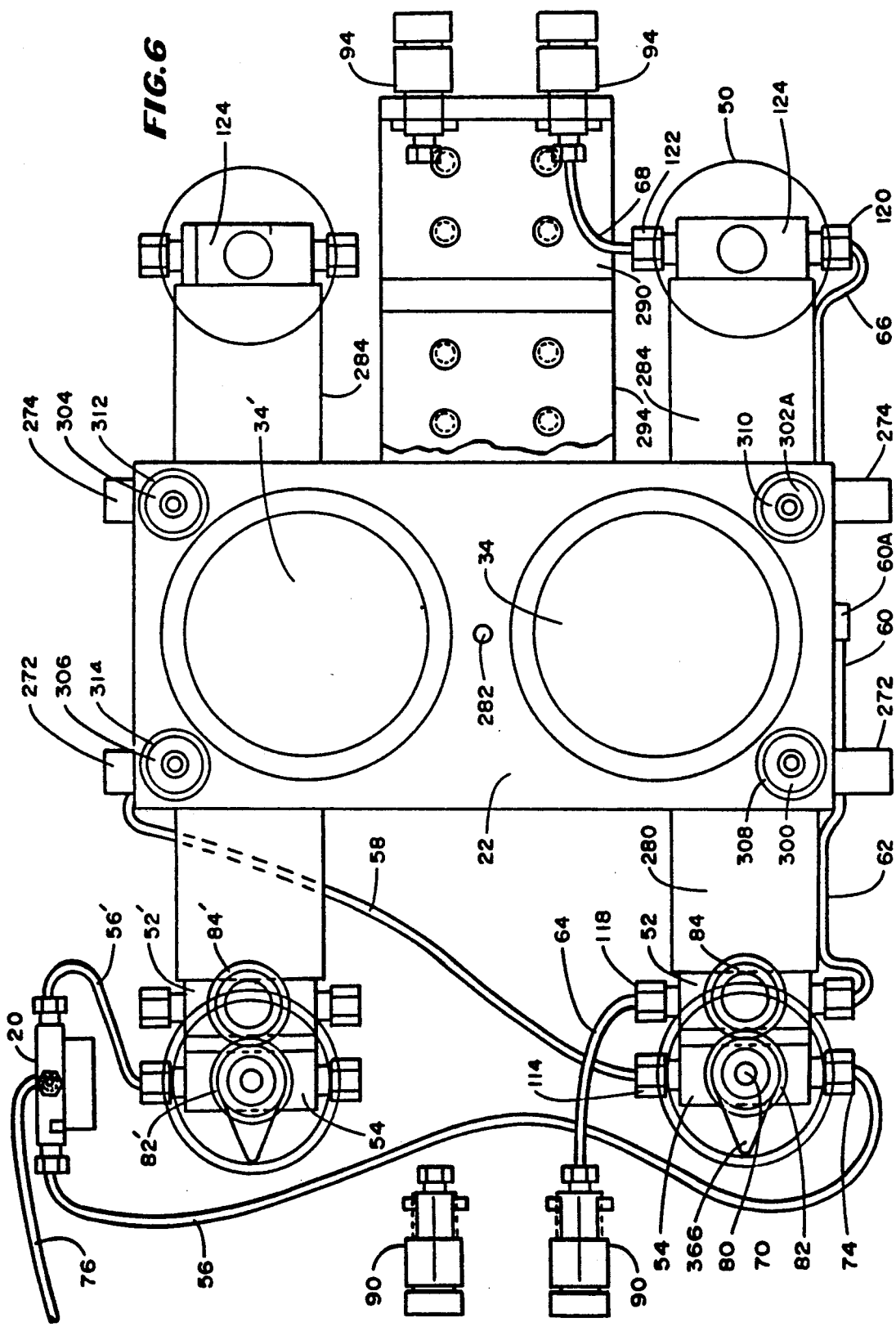
Figure 7:
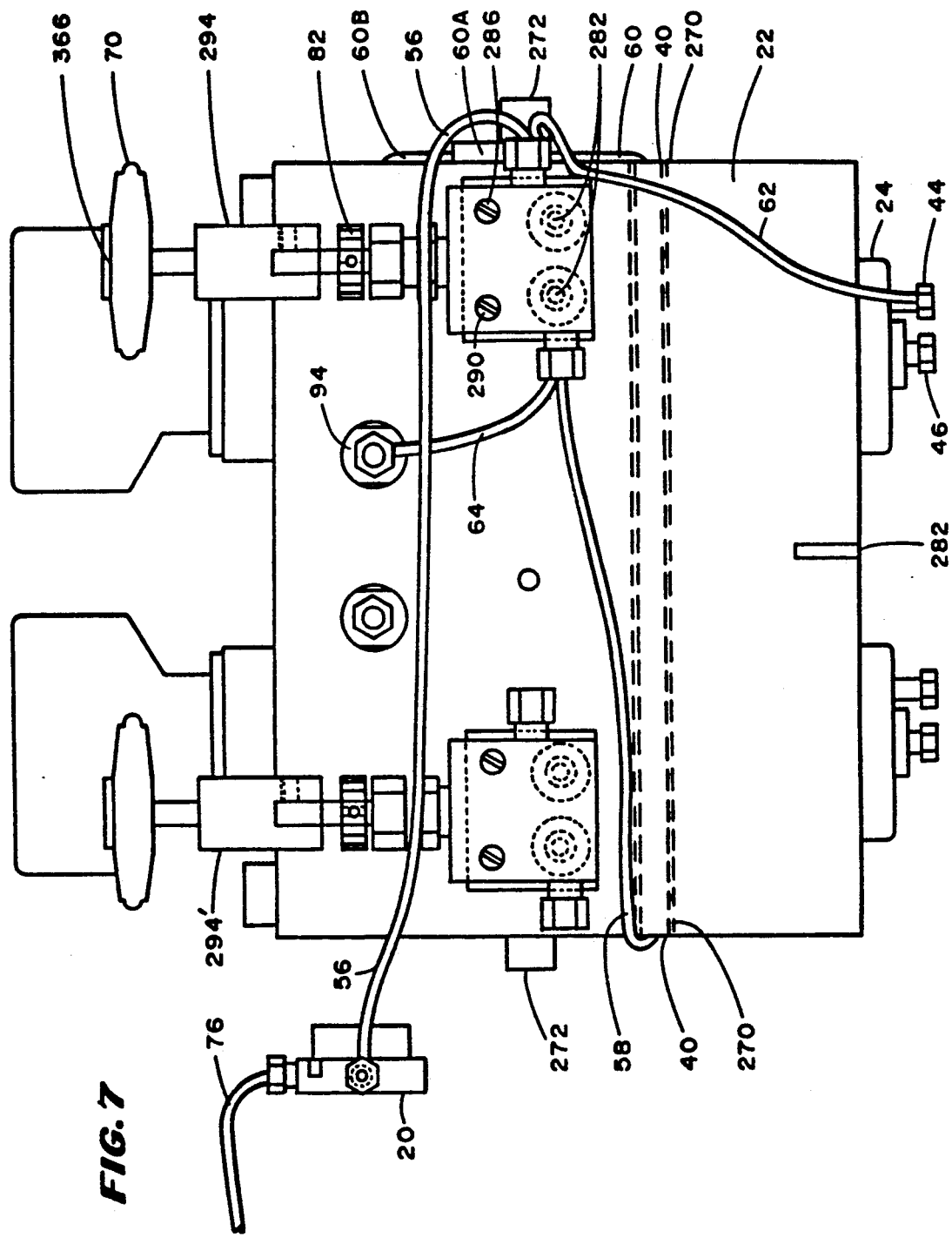
Figure 8:
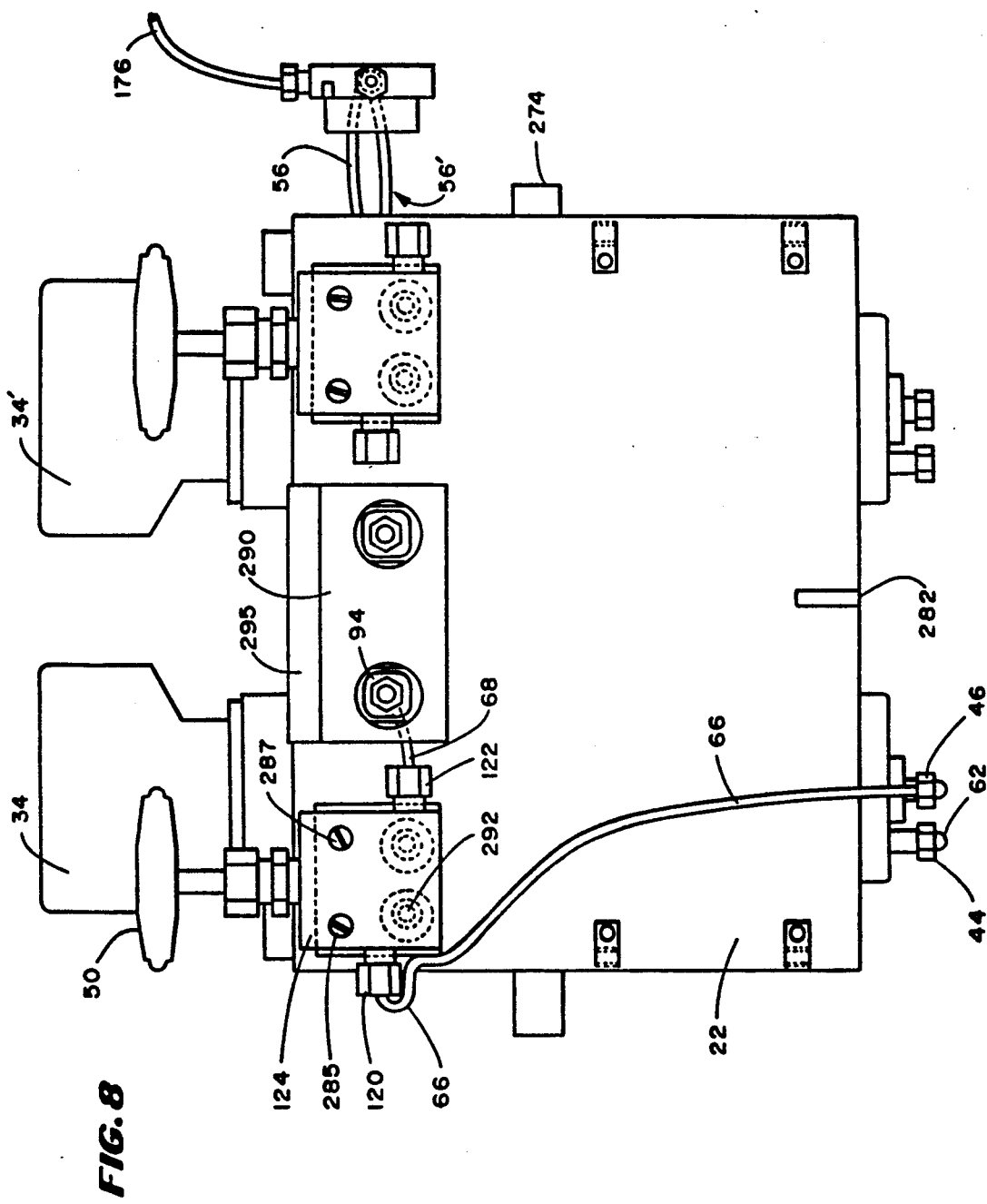
Figure 9:
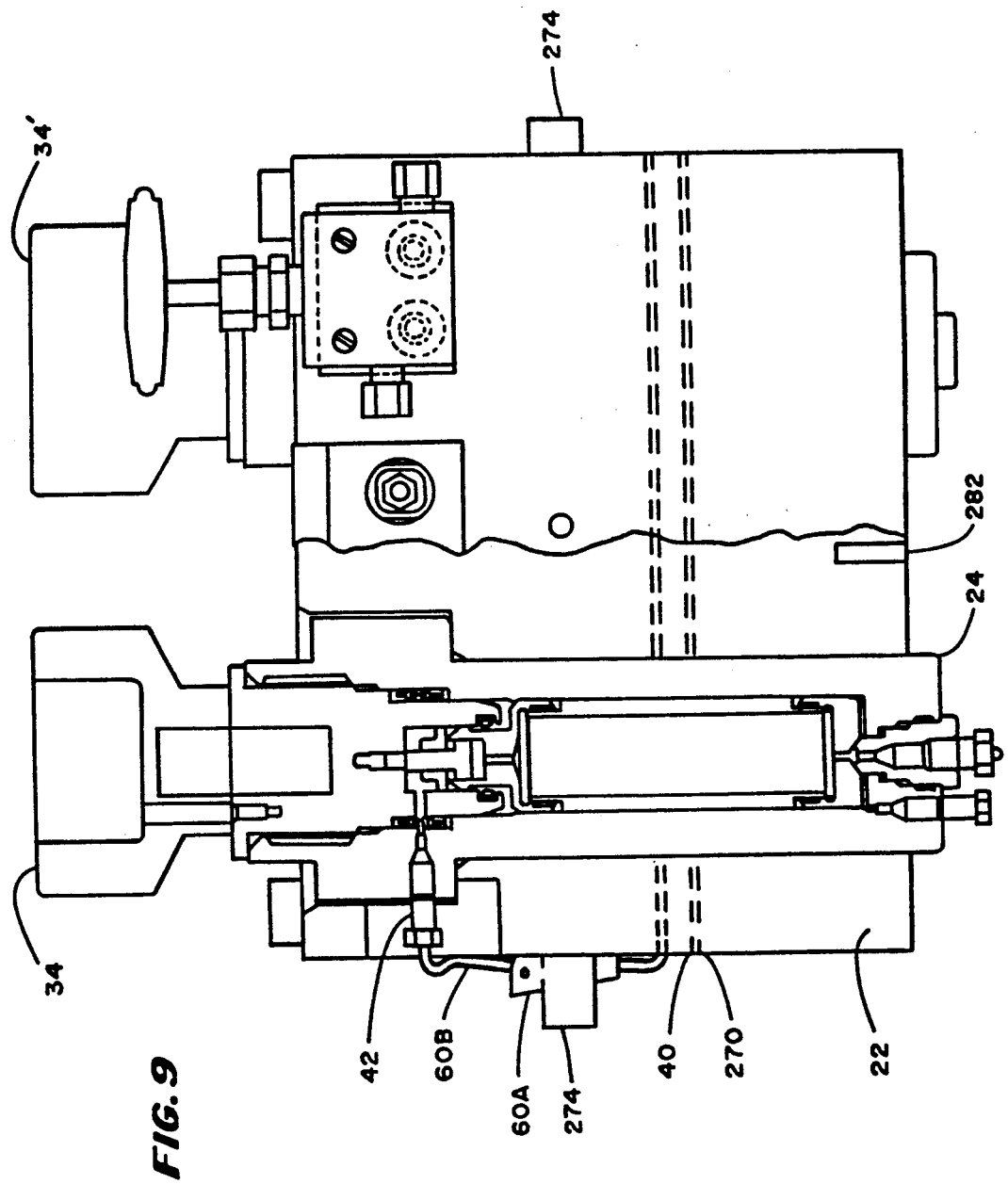
FIG. 9 is a partly sectional, partly broken away, right elevational fragmentary view of the supercritical liquid extraction system of FIGS. 5-8.

As best shown in FIG. 5, the heat exchanger 40 is located within bore 270 in heating block 22. The tube 58 enters this bore at one end, is coiled in a helix throughout the length of bore 270, and exits the other end as tube 60 which communicates with inlet fitting 42 of pressure vessel 24 within heating block 22. Tubular heating elements 272 and 274 are located within bores 276 and 278 and extend therewith throughout the length of heating block 22. They protrude from both ends of heating bloc 22 as shown in FIG. 6. In the preferred embodiment, these heating elements have a total heating power of 800 watts; 400 watts each.

Aluminum support block 280 is fastened to heating block 22 by cap screws 282 recessed within support block 280. Valves 54 and 52 are fastened to support block 280 by screws 286 and 290, and the valves are separated by spacer 292. Support block 280 is thermally conductive and heats valve 52 to a temperature near that of the heating block 22.

Aluminum support block 284 is held to heating block 22 by cap screws 292 recessed within support block 284. The body of valve 124 is screwed to support block 284 with screws 285 and 287. The high thermal conductivity of support block 284 heats valve 124 to approximately the temperature of heating block 22. The tube 68 leads from valve 124 to outlet fitting 94. Outlet fitting 94 is heated to a temperature near that of heating block 22 because it is mounted to aluminum angle 290 which in turn is mounted to aluminum plate 295 that is fastened to support block 284 shown in top view in FIG. 6. Support block 284 is screwed (fastening not shown) to heating block 22. Since support block 284, plate 295 and angle 290 are made of thermally conductive aluminum, heat from heating block 22 is efficiently conducted to fitting 94.

Tubes 60, 62 and 66 are routed in contact with heating block 22 or in contact with thermally conductive supporting members in contact with heating block 22. This keeps the tube and their contents sufficiently hot so that dissolved sample contents or contaminants do not condense or precipitate from solution in the supercritical fluid. The tube 68 is kept hot because of the location of the insulation to be described in FIGS. 10–14.

FIGS. 10–13 are a four-view orthographic projection of the outside cabinet enclosing the dual extraction system illustrated in FIGS. 5–9 with FIGS. 10 and being a front elevational broken away view and a plan broken away view respectively showing the dual extractor unit of FIGS. 5–9 mounted under cabinet top 296. As shown in FIG. 10, dual extraction unit is separated from the top of the cabinet 296 by the four tubular phenolic spacers 300 and 302, 304 and 306 (FIG. 6) two of which are shown at 300 and 302 in FIG. 10, which spacers extend into recesses 308, 310, 312 and 314 (FIG. 6) in the heater block 22 (FIGS. 5–9). Stainless steel screws 320, 322, 324 and 326 extend through the bores of the tubular spacers 300, 302, 304 and 306 (FIG. 6) into tapped holes 330, 332, 334 and 336 (FIG. 6) in heater block 22.

The stainless steel material of the screws 320, 322, 324 and 326 is a poor conductor of heat, and the phenolic spacers 300, 302, 304 and 306 (FIG. 6) are even poorer conductor of heat; thus thermally isolating the heating block 22, pressure vessel 24, breech plug 32, the valves, and other heated components from the cabinet cover 296.

As best shown by FIG. 4, the pressure vessel 24 and breech plug 32 are thermally isolated from the cabinet top 296 by plastic grommet 340 and air gap 342. Insulation 344 thermally isolates heater block 22, pressure vessel 24, all of the valves, connecting tube 68 and sample outlet fitting 94 from the cabinet top 296. The sample outlet fitting 94 is additionally isolated from cabinet top 296 by the radial gap between the fitting 94 and the clearance hole for it 348 within the cabinet top 296 (FIG. 13). Insulation 350 insulates all valves, heater block, pressure vessel 24, the tubes 60, 62, 66 and 68 from the lower outside environment so that they are kept hot by heat originating in the heater block 22.

FIG. 11 is a top view of the cabinet with the breech plugs 32 and 32' removed and with all the valve knobs removed. Grommeted holes from the two breech plugs are shown as 352 and 352'. Holes 354, 356, 354' and 356' are clearance holes for the operating shafts and other protruding parts of valves 54, 54' 124 and 124' respectively. The clearance holes are large enough so that cabinet top 296 does not touch any parts directly connected to the valves. Valves 54 and 54' are fitted with control shaft extension members 294 and 294' because of the additional space required by the gears 84 and 82 (and 84' and 82').

Thermocouple temperature controller 360 (FIGS. 10-13) provides time-proportioned power to heating elements 272 and 272' (FIGS. 5-9). The low energy time-proportioned output of thermocouple temperature controller 360 is used to control a conventional semiconductor switch or relay within the controller which in turn switches the power to the heating elements, which in the preferred embodiment is a total of 800 watts. The sensing thermocouple for providing temperature feedback information to thermocouple temperature controller 360 has an iron-constantan thermocouple junction located within bore 364 (FIGS. 5-9) of the heating block 22. Manual power switch 298 turns the heating circuit on and off. The thermocouple temperature controller, manual power switch and semiconductor switch or relay are loacted within the case bottom 362. Preferrably, a small colling fan located in the case bottom draws outside air through the case bottom.

Figure 14:
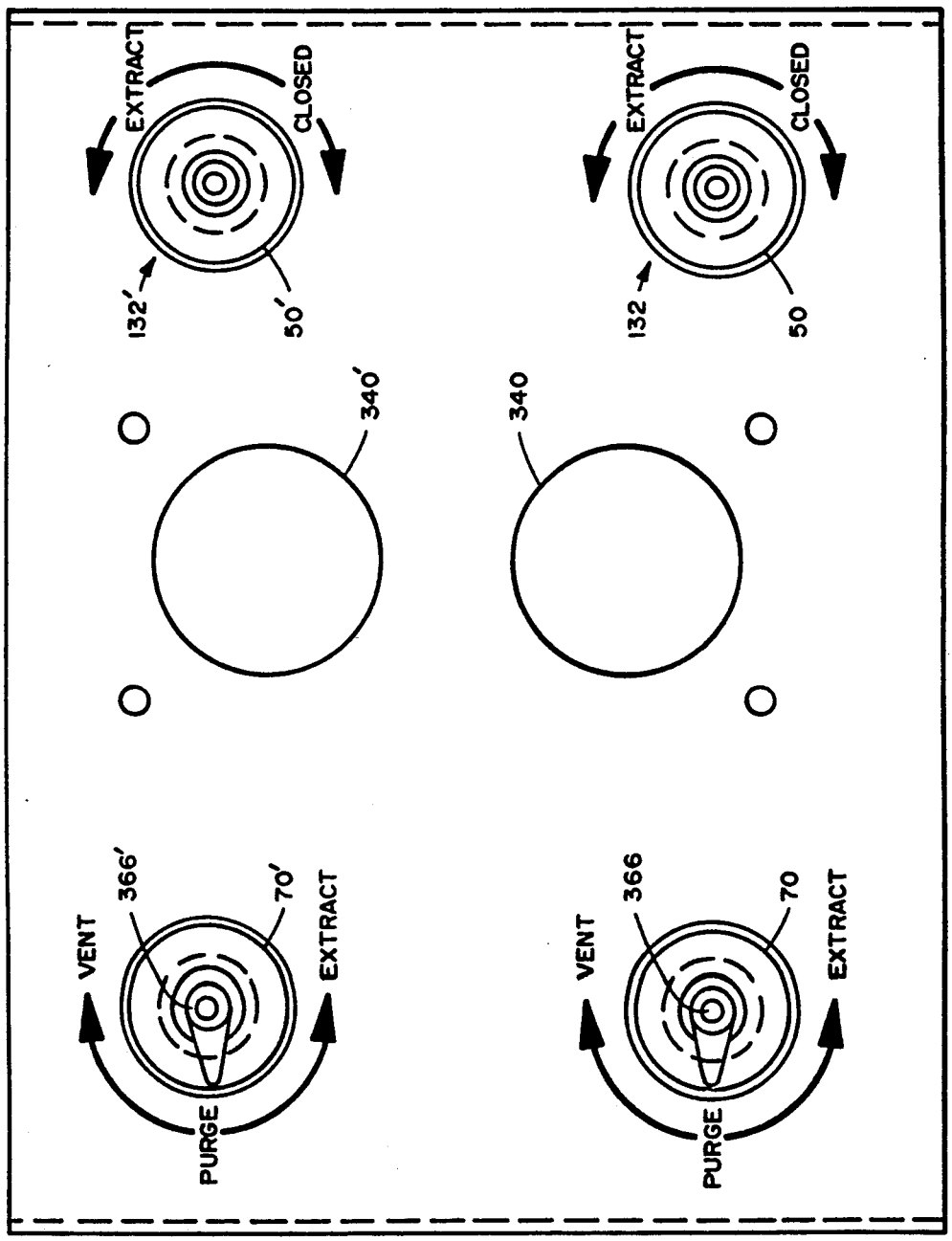
FIG. 14 is a plan view of a cabinet for the embodiment of FIGS. 1-13 illustrating the labeling of the control valves on top of the supercritical fluid liquid extraction system.

FIG. 14 is a top view of the cabinet showing the labeling of the control knobs for the valves. The geared dual valve 54 and 52 (and also 54' and 52' for the second extraction station) has knob 70 with indicating pointer 366. In the "PURGE" (middle) position shown, both valves 54 and 52 are open. In the fully clockwise position with the pointer indicating "VENT", valve 54 is closed and valve 52 is open. In the fully counterclockwise position with the pointer indicating "EXTRACT", valve 54 is open and valve 52 is closed. In regard to control knob 132 connected to valve 124 (and control knob 132' connected to 124'), clockwise rotation of the knob closes the valve and counterclockwise rotation (in the "EXTRACT" direction) opens the valve.

Before using the extraction system 10, the pump is set to the desired pressure and the heater block 22 is set to the desired temperature. The bottom cap 144 (FIG. 2) with the frit 160 is screwed onto the bottom of extraction tube 152. The internal cavity 158 is then filled or partly filled with sample to be extracted The frit 162 and top cap 174 are then screwed on to the top of extraction tube 152 forming the cartridge and plug assembly 26 (FIG. 3).

The cartridge and plug assembly 26 is then clipped into breech plug 32 by shoving the fitting nipple 176 on the extraction cartridge past garter spring 184 located within breech plug 32. Knob 70 and pointer 366 are set to the "VENT" position (FIG. 14) closing valve 54 and opening valve 52 (FIG. 1). Valve 124 is set to the clockwise ("CLOSED") position.

The assembled breech plug and extraction cartridge are inserted into preheated pressure vessel 22 and manually screwed with knob 34 into pressure vessel 24 until annular flange 190 contacts the top of pressure vessel 24 (FIG. 4) The pressure vessel has been preheated under control of thermocouple temperature controller 360 to the desired temperature. The cartridge and plug assembly 26 within pressure vessel 24 rapidly rises to the required temperature.

After insertion of the cartridge and plug assembly 26 into the sample block 24, valve knob 70 is rotated so that its pointer 366 is at the "PURGE" position. In tis position, both valves 54 and 52 are open. Since the pump 12 has already been set to the desired fluid pressure, fluid flows through tubes 76, 56, valve 54, tube 58, heat exchanger 40, tube 60, check valves 60A and 60B and inlet fitting 42 into the cavity 180 (FIG. 4). Since valve 124 is closed, supercritical fluid preheated to the correct temperature by heat exchanger 40, flows past hat-shaped washer 216, fitting nipple 176 and around the outside of cartridge and plug assembly 26 (FIG. 3). This supercritical fluid dissolves any contaminants on the outside of extraction cartridge assembly 30 and any contaminants inside pressure vessel 24. The hot supercritical fluid also insures that the extraction cartridge assembly 30 is at the proper operating temperature. The supercritical fluid flushes the contaminants from fitting 44, through tube 62, valve 52, tube 64, the fitting 90 and the capillary tube 110.

After a short purge cycle, control knob 70 is set so that its pointer 366 points to "EXTRACT" (FIG. 14). This sets valves 54 and 52 so that valve 54 is open and valve 52 is closed. Immediately after making this setting, the operator opens valve 124 by rotating knob 132 counterclockwise in the "EXTRACT" direction indicated on FIG. 14. Pressurized fluid flows through valve 54 into heat exchanger 40 so that it is at the desired supercritical temperature, and flows into fitting 42. It then flows into cavity 180 and past the annular space between shoulder screw 218 and the inside diameter of hat-shaped washer 216, after which it passes through the interior of fitting nipple 176, through passageway 250 and into the extraction vessel 26 (FIG. 3). This supercritical fluid flowing through the interior sample cavity 254 (FIG. 2) of the extraction cartridge extracts analyte from the sample 134 contained within the cavity 254.

Supercritical fluid with the analyte in solution passes out through the fitting 46, the tube 66, the valve 124, the tube 68, the coupling 94 and the capillary tube 128 which leads into the collecting solvent 104 within test tube 98. The analyte is dissolved in the solvent 104 for later analysis When the extraction is complete knob 132 is rotated clockwise in the "CLOSED" direction, closing valve 124. This stops the flow of supercritical fluid into the extraction cartridge 26. Knob 70 is then rotated clockwise so that its pointer 366 is in the "VENT" position. This closes valve 54 and opens valve 52, depressurizing the pressure vessel 24 and cartridge and plug assembly 26 through capillary tube 110. When bubbles stop issues through the end of capillary tube 110, depressurization is complete Knob 34 is rotated counterclockwise to unscrew the breech plug 32 and the attached cartridge and plug assembly 26 from pressure vessel 24. Extraction cartridge assembly 30 may now be open to empty spent sample.

Figure 15:
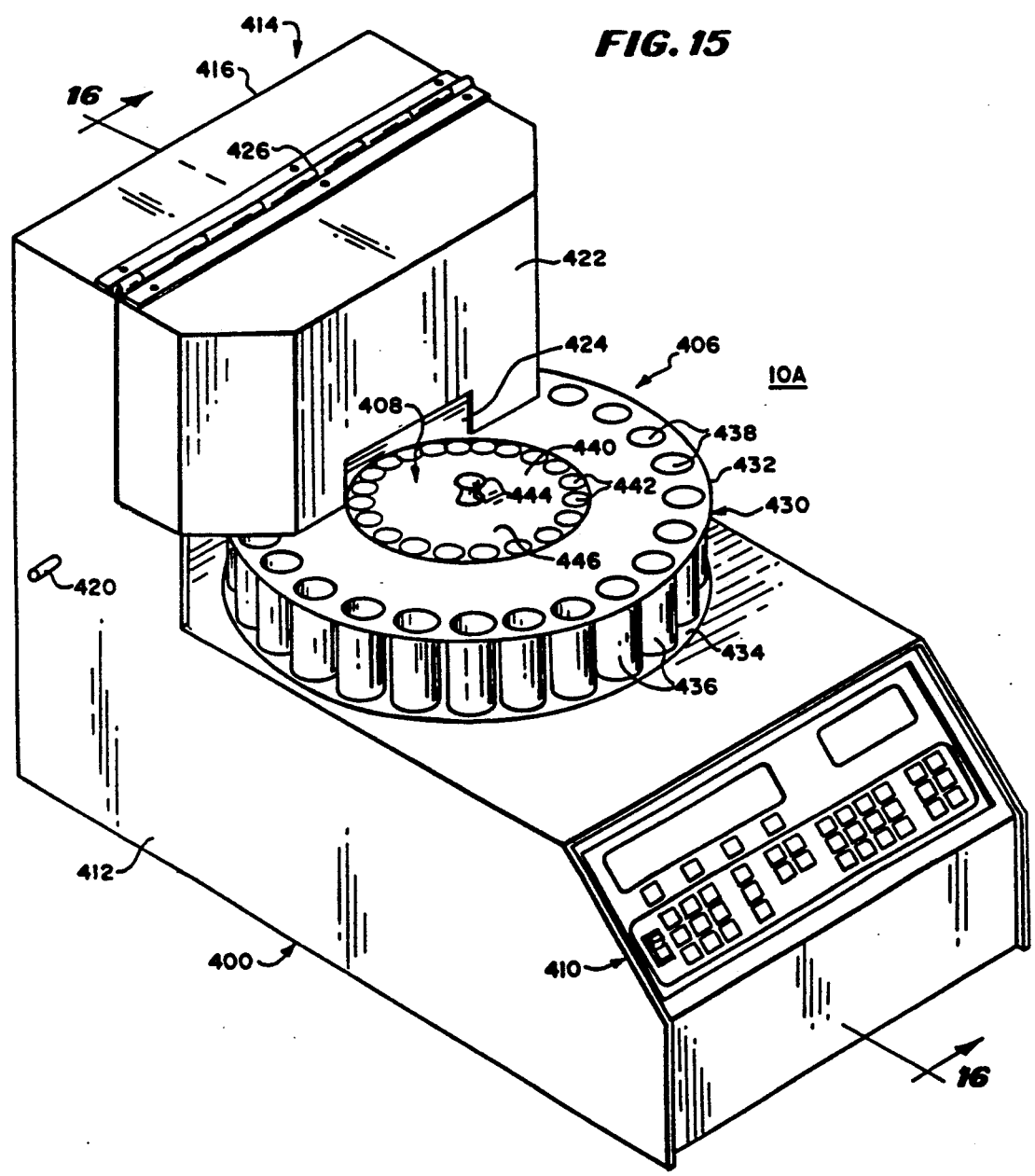
FIG. 15 is a perspective view of another embodiment of the invention capable of automatic extraction of a series of samples.

In FIG. 15, there is shown a simplified perspective view of another embodiment 10A of supercritical fluid extraction system having a cabinet 400 containing a drive section in its lower portion (not shown in FIG. 15), an extraction section in the upper portion of the cabinet (not shown in FIG. 15), a sample injection section 406 and a fraction collection section 408. The supercritical liquid extraction system 10A is controlled from a panel 410 on the front of the cabinet 400 and the drive section operates the extraction section, the sample injection section 406, and the fraction collection section 408, which cooperate together to extract a plurality of samples sequentially and collect the extractant from the samples in separate containers with minimum intervention by an operator.

The liquid extraction system in the embodiment 10A operates in a manner similar to that of the embodiment of FIG. 1 but is adapted to cooperate with the novel sample injector and fraction collector. With this arrangement, a series of samples to be extracted are preloaded into a means for holding the samples and the samples are automatically injected one at a time into the extractor. In the extractor, supercritical fluid is supplied to the samples and an extractant is removed from the samples one by one. To aid in correlating the embodiment 10 and the embodiment 10A, similar parts have the same reference numerals but in the embodiment of FIG. 10A, the numerals include the suffix "A".

The extractant is supplied to individual containers or individual compartments of one container in a fraction collector. Thus, a plurality of extractions are performed on a plurality of different preloaded samples without the need for manually loading samples or initiating the flow of the supercritical fluid for each individual sample. The samples are automatically mechanically moved one by one into the extractor for extraction instead of being individually physically injected by an operator.

The cabinet 400 has a lower portion 412 generally shaped as a right regular parallelopiped with an angled control panel 410 and upstanding upper portion 414 which is another right regular parallelopiped extending upwardly to create a profile substantially shaped as an "L" having a common back portion or rear panel 416 which may contain fans and connections for supplementary pumps and the like. A fluid fitting 420 extends from one side to permit near supercritical fluids to be introduced into the cabinet 400. The L-profiled cabinet 400 has an angled front panel 410 for convenient use of controls and a top surface on the foot of the "L" for manipulation of samples to be injected and extractants that are collected.

To permit access to the interior of the cabinet 400, the upper portion 414 includes a hinged front access panel 422 having hinges 426 at its top so that it can be pivoted upwardly. It includes an opening 424 near its bottom to permit the entrance of fraction collector receptacles that are relatively tall. It extends downwardly to a point spaced from the top surface of the lower portion 412 of the cabinet 400 a sufficient distance to permit the entrance of normal receptacles used in the sample injector and the fraction collector.

The sample injection section 406 includes a sample reel 430 which is formed of upper and lower rotatable plates 432 and 434 spaced vertically from each other and containing holes in the upper plate 432 and openings in the lower plate 434 which receive cylindrical tubular sleeves 436 having vertical longitudinal axes and open ends. The upper open end 438 permits samples to be received and to be removed as the sample reel 430 is rotated into the extractor.

With this arrangement, the sample reel 430 may be rotated to move samples one by one into the extractor for processing. The sample reel 430 is horizontal and extends into the upper portion 414 of the cabinet 400 and into the extractor assembly with its vertical center of rotation being outside of the upper portion 414 to permit ready access to a number of the sleeves 436 by users and yet to permit sequential rotation by automatic means into the extractor. In the preferred embodiment, there are 24 sleeves for containing 24 distinctly different samples which can, without human intervention, be moved into the extractor.

To receive extractant, the fraction collection section 408 includes a horizontal fraction collector reel 440 mounted concentrically with the sample reel 430 but having a smaller diameter to be inside the sample reel 430 having a plurality of openings 442 circularly arranged in spaced apart relationship with each other about the periphery of a top plate 446 of the fraction collector reel 440 and having in its center a knob 444 by which the fraction collector reel 440 may be lifted and removed from the cabinet 400. With this arrangement, the fraction collector reel 440 may be lifted and removed or reinserted after the hinged access panel 422 is pivoted upwardly about the hinges 426.

When the fraction collector reel 440 is in place, it is rotated automatically through the opening 424 into a location in which one or more individual containers 442 may receive extractant. The fraction collector reel 440 is moved alternately with the sample reel 430 and independently- of it so that, after a sample injection and extraction, one or more of the openings 442 are moved into position to receive the extractant prior to the injection of another sample for extraction.

Because the reels 430 and 440 rotate within the upper portion 414 of the cabinet 400 with a portion of its periphery outside of the cabinet 400, the collected extractant may be removed and new sample added during operation of the equipment. For this purpose, the receptacles for the fractions and the receptacles for the samples have upward open ends and are mounted with their axes vertical.

Figure 16:
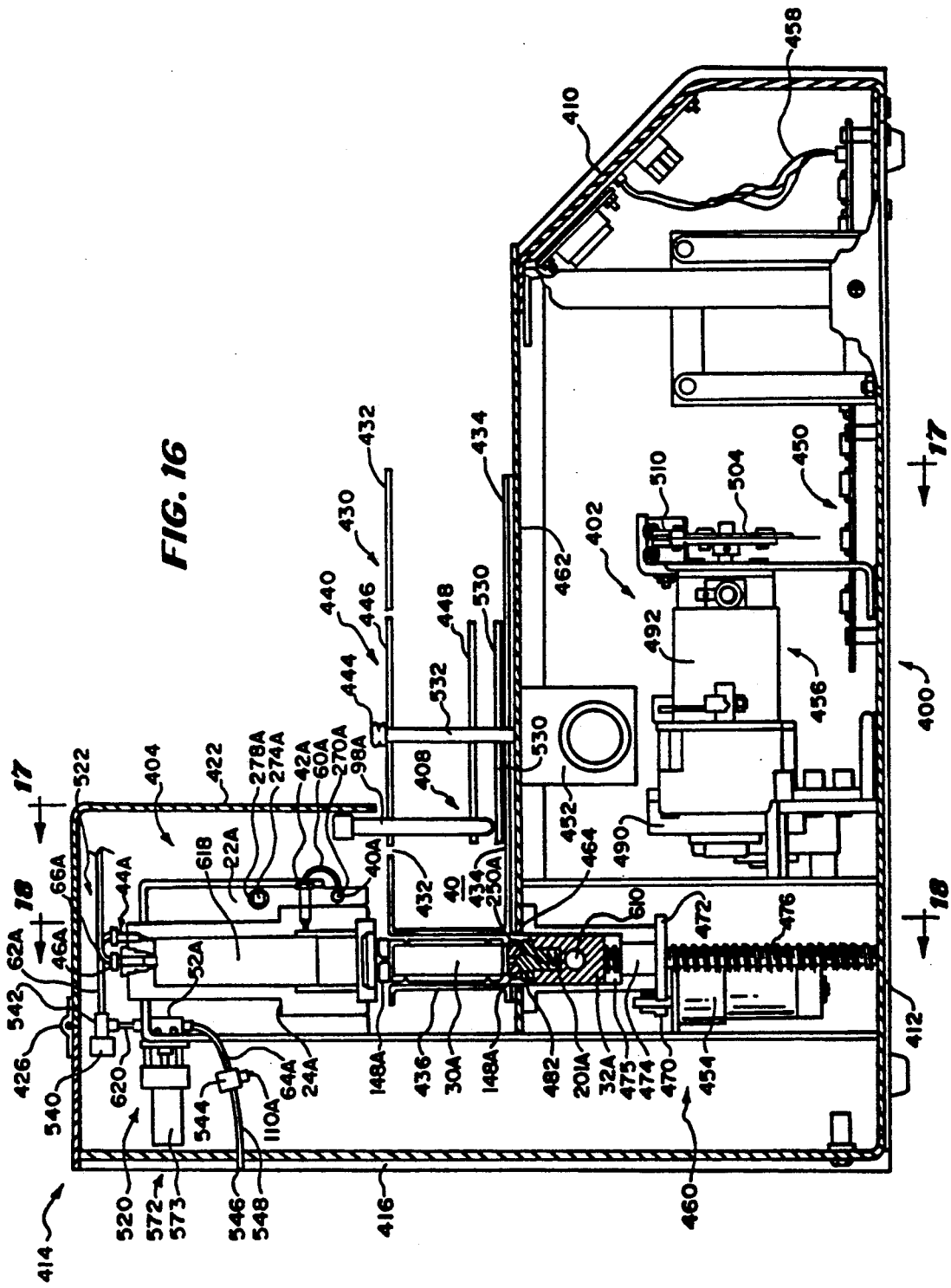
FIG. 16 is a sectional view taken through lines 16-16 of FIG. 15.

In FIG. 16, there is shown a longitudinal sectional view through lines 16—16 of FIG. 15 showing the cabinet 400, the drive section 402 within the cabinet 400, the extraction section 404, the sample injection section 406 and the fraction collection section 408. The drive section 402 includes a control system 450, a sample-and-extractant container reel drive assembly 452, a sample injector drive 454 and a fluid drive or pump 456. The control system 450 receives information from the control panel 410 and conveys information to it through a cable 458. It also controls the pump 456, the sample-and-extractant container reel drive assembly 452 and the sample injector drive 454, which cooperate together to move samples into position, inject them into the extractor, pump fluids through the extractor to extract the samples and collect the samples in sequence one by one.

To inject samples into the extraction section 404, the sample injection section 406 includes the sample-and-extractant container reel drive assembly 452, the sample reel assembly 430, and a cartridge injector assembly 460. The sample-and-extractant container reel drive assembly 452 drives the sample reel assembly 430 to carry a cartridge assembly 30A onto the cartridge injector assembly 460 which lifts it under the control of the sample injector drive 454 upwardly into a pressure vessel 24A for the purpose of extracting a sample within the cartridge assembly 30A. The cartridge assembly 30A and the pressure vessel 24A are similar to the cartridge assembly 30 and pressure vessel 24 of the embodiment of FIGS. 1–14 and are only adapted such as by having their top and bottom sides reversed to permit the cartridge assembly 30A to be inserted from the bottom into the pressure vessel 24A and be more easily sealed therein for extraction and removed by gravity after extraction.

To drive the sample reel assembly 430, the sample-and-extractant container reel drive assembly 452 includes a central transmission and motors on each side that drive the transmission under the control of the control system 450 to drive either one or both the sample injector reel assembly 430 and the fraction collector reel 440.

The sample injector reel assembly 430 includes the top plate 432, the bottom plate 434, both of which are rotatable together to carry a plurality of sleeves 436 sequentially, one at a time, into position for the repeated injecting of cartridges one by one into the pressure vessel 24A and the removal of the cartridges from the pressure vessel 24A and the return of them to the reel assembly 430 one by one so that only one cartridge is in the pressure vessel 24A at a time.

Within the extraction section 404, a stationary bottom plate 462 has a hole 464, with the hole being aligned with the open-bottom end of the pressure vessel 24A and the upper end of the cartridge injector assembly 460. Consequently, the cartridge assemblies such as 30A are rotated one by one above the open end 464 in the bottom plate 462 for movement upwardly into the pressure vessel assembly 24A by the cartridge injector assembly 460 under the control of the sample injector drive 454 for extraction of the sample therein. With this arrangement, a stationary plate 462 holds the cartridge assemblies 30A in place as they are rotated by the upper and lower plates 432 and 434 until they are sequentially brought over the opening 464 through the stationary plate 462 for elevation into the pressure vessel 24A.

To inject cartridges into the pressure vessel 24A, the cartridge injector assembly 460 includes the sample injector drive 454, a pinion 470, a gear 472, a multi-threaded, fast action nut 474, a corresponding screw 476, and piston or plug 32A. The pinion 470 is mounted to the output shaft of the drive gear motor 454 and engages the teeth of gear 472. The gear 472 is fastened to or integrally formed with the drive nut 474 which, as it rotates, moves the screw 476 upwardly or downwardly. The support platform 475, piston or plug 32A and sample container 30A are carried by the top of the screw 476 and are moved upwardly and downwardly. The top surface of the plug 32A, which is supported by the screw 476 in its lower position is flush with the bottom of the opening 464 in the fixed plate 462 to support a cartridge such as 30A therein and in its top position positions the piston or plug 32A at the bottom of the pressure vessel 24A. Plug 32A carries self-actuated, spring-biased, cylinder seals, such as those made by the Bal-Seal Corporation. These seals provide a high pressure fluid-tight seal between the plug 32A and the inner wall of the pressure vessel 24A.

With this arrangement, the piston or plug 32A is sealable against the walls of the pressure vessel 24A during the extraction process after moving the cartridge assembly 30A upwardly into the pressure vessel 24A, and after extraction, can move the cartridge assembly 30A downwardly back to the sample reel assembly 430 for rotation out of the upper injector housing 414 as a new cartridge is moved into position for injecting into the pressure vessel 24A. A bearing mount rotatably supports the nut 474 while maintaining it in the same vertical position so as to move the rapid-advance screw or other screw 476 upwardly and downwardly.

The plug 32A serves a function similar to the breech plug 32 in the embodiment of FIGS. 1–14 and contains within it an opening supporting a spring 201A and a support block 482 so that the support block 482 is biased inwardly against the cartridge end 148A to move the cartridge 30A into place against fittings for supercritical fluid.

To extract the sample in the cartridge 30A after it has been moved into position and the breech plug 32A fastened in place for a seal, extracting fluid is applied through the fitting 42A in a manner similar to the embodiment of FIG. so that the extracting fluid flows through one path into the cartridge 30A and through another path over the outside of the cartridge 30A into the fitting 44A and from there to a purge collector or vent. The extractant, after passing through the cartridge and the sample, exits from a fitting 46A and proceeds to the sample collector in a manner to be described hereinafter.

To pump fluid such as carbon dioxide into the pressure vessel 24A at a temperature proper for supercritical extraction: (1) the pump 456 includes a pump head 490 and an electrical motor 492; and (2) the pressure vessel 24A has an aluminum heating block 22A over it, an opening 278A in the aluminum heating block, a rod-shaped heating element 274A in the aperture 278A, the extracting fluid fitting 42A and a heat exchanger 40A entering the aluminum heating block 22A at aperture 270A. The motor 492 drives the pump mechanism 490 to pump fluid into the aperture 270A, through the heat exchanger 40A within the aperture 270A, through the connecting tubing 60A and the fitting 42A and into the cartridge 30A and the pressure vessel 24A. The aluminum block 22A controls the temperature of the fluid, which may be carbon dioxide or any other useful extracting fluid to keep it above the supercritical temperature for that fluid and for that purpose, the heating rod 274A within the aperature 278A is used when necessary to heat the aluminum block 22A.

The pump 456 may be any suitable pump, but an appropriate pump for carbon dioxide is the pump used in the Isco model 2350 HPLC Pumping System sold by Isco, Inc., Lincoln, Nebr. However, for best results when using carbon dioxide, the stroke of this pump is modified from ten millimeters to fifteen millimeters, and smaller, lower trapped-volume check valves are used. These modifications increase the compression ratio of the pump from 1.7:1 to 2.6:1 and increase the displacement by a multiple of 1.5. An additional change is to use Carpenter Technologies 182FM stainless steel in the pump head, instead of type 316, for better thermal conducting.

To collect extractants, the fraction collector section 408 includes the fraction collection reel 440, the sample-and-extractant container reel drive assembly 452, a purge fluid outlet system 520 and an extractant fluid outlet system 522. The fraction collection reel 440 moves receptacles such as 98A into position within the housing 414 where the extractant fluid outlet system 522 to be described in greater detail hereinafter causes fluid from the fitting 46A in the pressure vessel 24A to flow outwardly and into the receptacle 98A after piercing a seal therein. The purge fluid system 520 causes purge fluid to flow from the purge fluid fitting 44A to a pressure control unit and finally to an exhaust or collection unit.

To move the collection receptacles 98A into position, the fraction collection reel 440 includes a knob 444, an intermediate plate 448, an upper plate 446, a lower disk plate 530 and a drive rod 532. The drive rod 532 rotates within the fixed disk 530 and carries above them the upper and lower plates 446 and 448. The upper and lower plates 446 and 448 have aligned circumferentially spaced holes through them, each of which can receive a collection vial such as 98A. The lower disk 530 does not have holes and supports the plates as they are moved. The knob 444 may be used to lift the fraction collector reel 440 from the center of the sample injector reel 430 after the hinged front access panel 422 has been opened about its hinge 426.

The sample-and-extractant container reel drive assembly 452 moves the collection vials one by one inside the upper portion of the housing 414 to receive extractant. One or more such vessels 98A may be moved in place each time a sample cartridge 30A is extracted so that the receptacles 98A are moved alternatively with the sample cartridges 30A, although several receptacles 98A may be moved in the time between moving one of the sample cartridges 30A into a pressure vessel 24A and the time the sample cartridge is removed from the pressure vessel 24A. The extractant passes through fitting 46A and into the fraction collector receptacles 98A in a manner to be described hereinafter.

The purge fitting 44A communicates with the extraction volume in the cartridge 30A and is connected to a Tee-joint tube 542 through tubing 62A. A second arm of the Tee-joint tube 542 is connected to an over-pressure safety diaphram 540 calibrated to burst at 12,500 pounds per square inch. This is an excess of the maximum rated working pressure of 10,000 pounds per square inch for pressure vessel 24A. The remaining arm of the Tee-joint tube 542 is connected to the purge valve 52A. The other side of the purge valve 52A is connected to the first side of a second Tee-joint tube 544 through the tube 64A. The second side of the Tee-joint tube 544 is connected to an exterior vent port 546 through a tube 548. The third arm of the Tee-joint tube 544 is connected to the exhaust tube 110A which vents the fraction collection vial 98A. With this arrangement, the purge fluid flowing through fitting 44A is removed and a tube connected to the vent port 546 is also used to vent the sample receptacle 98A in a manner to be described hereinafter.

Figure 17:
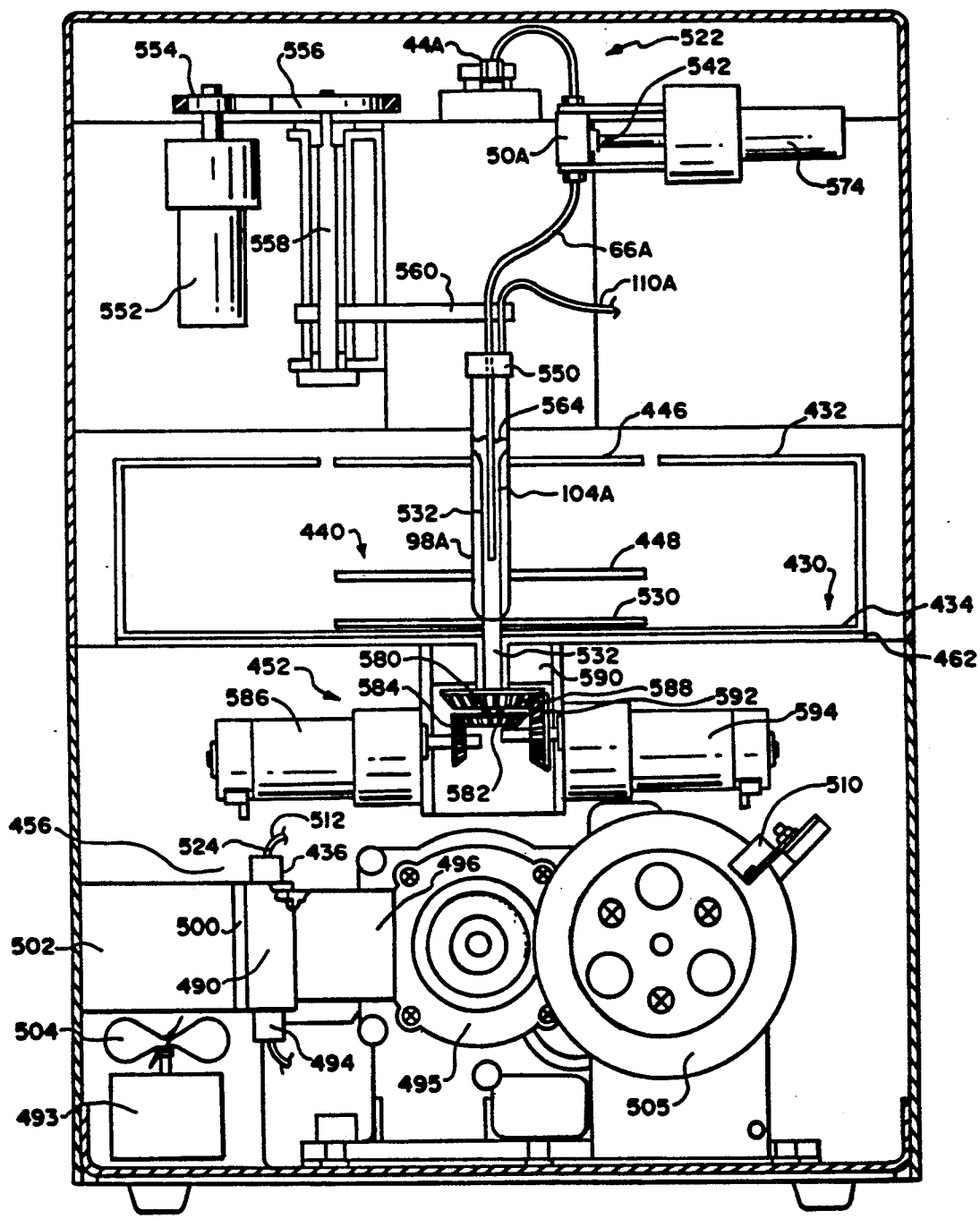
FIG. 17 is a sectional view taken through lines 17—17 of FIG. 16.

In FIG. 17, there is shown a simplified sectional elevational view of the embodiment 10A of supercritical fluid extractor taken through lines 17-17 of FIG. 16 having the sample-and-extractant container reel drive assembly 452, the pump 456 and the extractant fluid outlet system 522. The sample-and-extractant container reel drive assembly 452 may selectively move either the sample reel 430 or the fraction collection reel 440 under the control of the controller 450 (FIG. 16).

To selectively drive the fraction collection reel 440, the sample-and-extractant container reel drive assembly 452 includes a fraction collection spindle 532, a tubular shaft 580, a bevel gear 582, a bevel gear 584 and a gear motor 586. The controller 450 controls the gear motor 586 to rotate the fraction collection reel 440. For this purpose, the spindle 532 is held by the tubular shaft 580. The bevel gear 582 is fastened at the end of the spindle 532 and meshes with the bevel gear 584 on gear motor 586. The controller 450 moves these gears into meshing position and causes the motor 586 to rotate its output shaft so as to drive the collection reel 440 (FIGS. 15 and 16) and not the sample injector reel 430 (FIGS. 15 and 16).

To move the sample injector reel 430, the sample-and-extractant container reel drive assembly 452 includes the tubular shaft 580 supported by bearing block 590, fraction collection spindle 532, bevel gear 588, bevel gear 592 and gear motor 594. The controller 450 actuates gear motor 594 to cause the bevel gear 592 to rotate. The bevel gear 592 meshes with the bevel gear 588 which is attached to the bottom end of the fraction collection spindle 532.

To cause extractant to flow into the fraction collection vial 98A, the extractant fluid outlet system 522 includes a gear motor 552, a pinion 554, a gear 556, a lead screw 558, an arm 560, and a restrictor tube 66A. The vials 98A have a seal 550 over the top, which seal can be pierced.

To cause the seal 550 to be pierced and extractant to flow into the vial 98A, the controller 450 starts the gear motor 552 which rotates its pinion 554 which is in engagement with the gear 556. The pinion 554 rotates the gear 556, which engages and is fastened to the rotating lead screw 558. The arm 560 is mounted for movement by the lead screw 558 and lowers it into a position where the restrictor tube 66A pierces the cap 550 on the collection vial 98A and moves its tip below the surface 564 of the collection fluid within the vial 98A. As the extractant flows into the tube, exhaust is removed from the tube through an exhaust tube 110A (FIG. 16 in addition to FIG. 17).

If either the tube 66A or the tube 110A are stiff or otherwise inconvenient to bend, it is advantageous to raise the collecting vial 98A up to tubes 66A and 110A, instead of lowering the tubes into the collecting vial. This alternate arrangement does not pose any difficulty as the collecting vial 98A may be raised by a support similar to plug 32A, which support is connected directly to plug 32A so that it moves synchronously with plug 32A.

With either arrangement, extractant flows through the fitting 46A (FIG. 16) from the sample cartridge 30A (FIG. 16) through the tubing 522 (FIG. 16), the valve 50A and the restrictor tube 66A. Extractant residing in bubbles from the tube are captured through trapping fluid 104A whereby extractant is trapped in the trapping fluid 104 in the vial 98A and extracting fluid passes out through the exhaust tube 110A, Tee-joint tube 544 (FIG. 16), tube 66A and exhaust port 546 (FIG. 16). After collection of the extractant, the motor 552 moves in the reverse direction and raises a rm 560 which removes the restrictor tube 66A and exhaust tube 110A from the vial 98A.

Because the pump head 490 is heated by pumping at high compression, both the pump head 490 and incoming fluid line are preferably cooled. In the preferred embodiment, they are cooled thermoelectrically (Peltier effect) and the pump head 490, the inlet check valve housing 494 are formed of Carpenter 182FM stainless steel rather than type 316 stainless steel to increase their thermal conductivity.

In pumping, the pump drive motor 492 (FIG. 16) drives a cam within cam housing 495 through appropriate gear train within the gear housing 496. The rotating cam within the cam housing 495 operates a pump plunger which cooperates with the pump head 490 (FIG. 17) to draw liquid carbon dioxide through inlet check valve assembly 494 and discharge it through outlet check valve assembly 436. The Peltier cooling plate 500 is mounted to the flat face of the pump head 490 (FIG. 17) with cooling fins 502 mounted for good thermal contact to the opposite side of the Peltier cooling plate 500.

When an electric current is passed in the proper direction through the Peltier cooling plate 500, heat is withdrawn from the pump head 490 (FIG. 17) and rejected into the cooling fins 502. A fan 504 driven by an electric motor 493 (FIG. 16) withdraws heat from the fins 502. Another Peltier-effect cooled heat exchanger is also utilized in the inlet line.

To control the speed of the motor 492 (FIG. 16), a tachometer wheel 505 is mounted to the shaft of motor 492 (FIG. 16) with a photoelectric tachometer sensor 510 mounted to provide signals reading indicia on the wheel. The signals from the photoelectric tachometer 510 indicate the speed of motor 492 and thus the pumping speed of pump 456. These signals are compared in the controller 450 and utilized to control the speed of the motor 492.

To control the pressure on the outlet line 512 from the pump, a pressure transducer 514 (FIG. 18) generates a signal indicating the pressure This signal is used as a feedback signal to control the pumping speed. This structure is provided by existing pumps such as the Isco model 260D pump.

Figure 18:
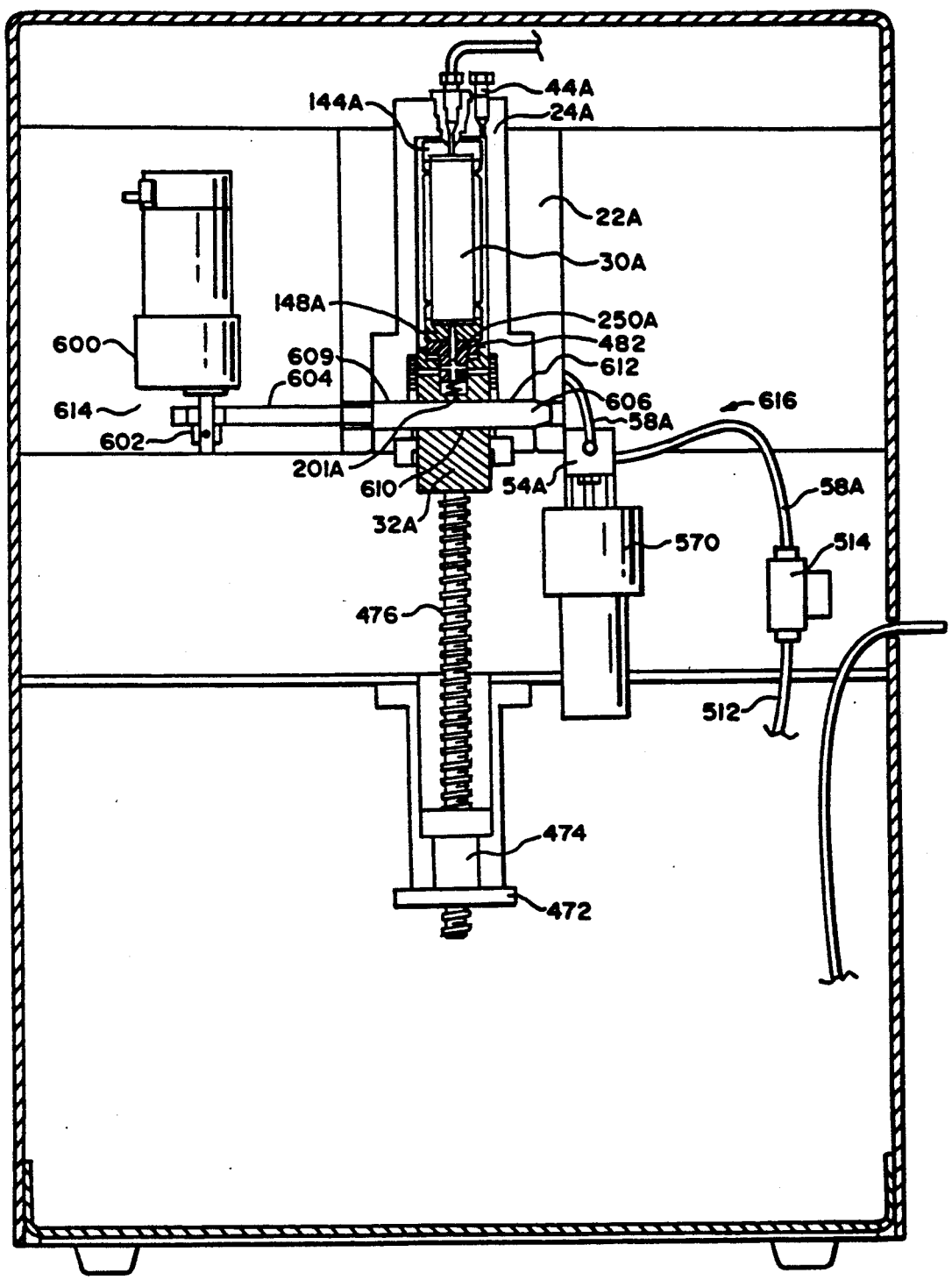
FIG. 18 is a sectional view taken through lines 18—18 of FIG. 16.

In FIG. 18, there is shown a sectional view, partly simplified, taken through lines 18—18 of FIG. 16 having a locking mechanism 614 for locking plug 32A into the pressure vessel 24A and a control mechanism 616 for controlling the extraction fluid. As best shown in this view, the locking mechanism 614 includes a gear motor 600, a pinion 602, a rack 604, a locking pin 606, a hole 609 in the pressure vessel 24A and a hole 610 in the piston or end piece or breach plug 32A and a hole 612 through the other side of the pressure vessel 24A. Instead of a pin 606, a yoke of the type conventionally used as a Winchester 94 rifle locking mechanism advantageously may be used. This type of locking mechanism is a yoke mounted to a pinion 602 and rack 604 as shown in FIG. 18. In this mechanism, a plate with a slot cut out of it to form a yoke is moved by the rack and pinion to pass under the plug 32A to hold it against pressure and provide strong support therewith by further engaging slots in the pressure vessel 24A. The aforementioned slot in the plate provides clearance for the screw 476.

In operation, the gear motor 600 is caused by the control system 450 (FIG. 16) to drive locking pin 606 through the opening 609 in the pressure vessel 24A, through the opening 610 in the piston 32A and through the opening 612 in the pressure vessel 24A by rotating the pinion 602 to drive the rack 604 that carries the locking pin 606, thus locking the cartridge 30A (FIG. 16) in place within the pressure vessel 24A.

To control the flow of extracting fluid from the pump 12 (FIG. 1) into the pressure vessel 24A and cartridge 30A, the control mechanism for extracting fluid includes the gear motor 570 and valve 54A that is connected at one end to the conduit 58A that extends from line 512 and pressure transducer 514 to the conduit 58 which passes into the heat exchanger 40 (FIG. 1). In operation, the gear motor 570 under the control of the control system 450 opens the valve 54A to permit the flow of extracting fluid into the cartridge 30A and pressure vessel 24A during an extraction operation. It also rotates in the opposite direction after extraction is complete to close the valve 54A.

The sample cartridge 30A (FIG. 16) is composed of a tubular sleeve or body portion 140A (FIG. 16) and end pieces 144A (FIG. 16) and 464A (FIG. 16). The end pieces 144A and 464A are made of stainless steel or an inert plastic and carry a stainless steel frit or filter disk centered in the interior of each. The flat, narrowed ends of the tubular sleeve 140A seal against PTFE washers around the frits which seal against the end pieces at the location between the diameters of the filter disks and the inside diameters of the end pieces 144A or 464A respectively.

In operation, a program is entered into the control panel 410 (FIG. 16) . This program is then stored in controller 450 and controls sample changing, fraction collection, static and/or dynamic extractions, fluid pressure, the steps or ramps of pressure, the supercritical fluid temperature, the elevation of the sample cartridge from the sampler reel up to the extraction chamber and return back to the sampler reel after extraction, locking and unlocking of the extraction chamber and operation of the three motor-operated valves in the manner described above to automatically duplicate the hand-operated functions of the embodiment of FIGS. 1-14. In the alternative, the operations may be initiated from the keyboard by manually closing circuits to the motors as required to perform the desired sequence.

At the start of an extraction cycle, the extraction fluid valve 54A, purge valve 50A (FIG. 17), and the extractant valve 52A (FIG. 16) are closed. The sample reel 430 brings a selected extraction cartridge 30A into position under the extraction chamber 618 (FIG. 16). The extraction sample cartridge 30A within a sleeve 436 on reel 430 is positioned above the single hole 464 in the disk 462 and is supported on a spring-loaded support block 482 within the top of the piston 32A.

To move the sample cartridge 30A into the extraction volume 618, the gear motor 454 causes the screw 476, piston 32A and cartridge 30A to rise to the position shown in FIG. 18, inserting cartridge 30A and piston 32A into the pressure vessel 24A.

To lock the sample cartridge in position, the gear motor 600 drives the pin 606 through the hole 609 in the pressure vessel 24A through the hole 610 in the piston 32A and through the hole 612 in the pressure vessel 24A. This locks the piston into position within the pressure vessel 24A.

To remove extractant, the spring 201A under the block 482 (FIG. 16) forces the block 482 to push the sample cartridge 30A up against the bottom of the fitting 46A (FIG. 16). The gear motor 552 lowers the arm 560 carrying the restrictor tube 66A and the rack 604 into the position shown in FIG. 17, puncturing the cap 550 on the collection tube 98A. The gear motor 570 rotates, opening the extraction fluid valve 54A, admitting extraction fluid through the heat exchanger 40A, tube 60A and the fitting 42A.

The extraction fluid flowing through the fitting 42A enters the bottom of the extraction cartridge 30A and permeates the sample within it. If it is suspected that the outside cartridge 30A may be contaminated, the purge valve 52A is opened at this time under the control of the gear motor 573. This purges or flushes the space between the outer wall of the sample cartridge 30A and the inner wall of the pressure vessel 24A. Flushing fluid leaves the extraction chamber 618 outside of the cartridge 30A through the purge fitting 44A, tube 62A, Tee-joint tube 542, tube 620 (FIG. 16), Tee-joint tube 544, tube 548 and vent port 546.

After purging, the gear motor 573 closes the purge valve 52A, terminating the purge operation. At this time, the controller 450 activates the gear motor 574 (FIG. 17) which opens the extractant valve 50A. Extractant fluid flows through the cartridge 30A, extracts material from the sample within the cartridge 30A, flows through the fitting 46A, tubing 62A, extractant valve 50A, and to the restrictor tube 66A. The restrictor tube 66A has a capillary bore of small enough diameter to maintain the desired extraction pressure at the desired extraction fluid flow rate.

In case the extraction cartridge is not completely full of sample, it is beneficial to flow the extractant fluid downward through the cartridge 30A instead of upwards as in the foregoing example. Downward flow of extractant is accomplished by permitting the extractant to flow into the cartridge through fitting 46A and from the cartridge through fitting plug 32A and the fitting 42A.

After extraction is complete and the extractant is collected in the trapping fluid 104A within the vial 98A, the gear motor 570 shuts the extraction fluid valve 54A. The gear motor 573 opens the purge valve 52A rapidly discharging the pressure and the extraction volume 618 The gear motor 574 closes the extractant valve 50A and the gear motor 552 raises the arm 560 and restrictor tubing 66A and exhaust tubing 110A. The gear motor 600 withdraws pin 606 from the holes 609, 610 and 612 in the pressure vessel 24A and the piston 32A.

After the piston has been unlocked, the gear motor 573 lowers the piston and sample cartridge 30A so that the sample cartridge 30A is lowered from being within the extraction volume 618 to being within the sleeve 436 of the sample reel 430 The gear motor 570 closes the purge valve 54A.

After the valves have been closed and the sample cartridge 30A returned to the sample reel, the sample reel 430 and the fraction collector reel 440 advance to bring another sample cartridge in another fraction collector vial into position Alternatively, multiple extractions on the same cartridge may be made by leaving the sample cartridge 30A in place and advancing only the collection reel The cycle of opening the valves and extracting is then repeated until the number of extractions from the single sample cartridge 30A have been made and the extractant deposited in a number of successive collection vials.

As can be understood from the above description, the supercritical extraction technique has several advantages: (1) it is more convenient than prior art extractors; (2) it includes a self-cleaning feature; (3) it has, as one component, a disposable inexpensive cartridge; and (4) in one embodiment, a series of samples can be extracted within minimum human intervention and the extractant collected in a fraction collector.

One reason it is convenient to use is because the cartridge containing the spent sample can be removed while the cartridge is hot because the sample cartridge has ample time to cool as it resides in the sample changer reel after extraction. Another reason it is convenient to use is that it is easier to open the cartridge and pressure vessel since there are no bolts or the like, and in some embodiments, the cartridge is disposable. This convenience is significant because it reduces the time of extraction materially.

It is less expensive because there is pressure equalization within the extractor and the pressure vessel even though it permits purging of the pressure vessel and extraction through separate outlets A reduction in cost is obtained because plastic cartridges or weaker metal cartridges may be used since the cartridge does not have to withstand a high pressure difference.

Although a preferred embodiment of the invention has been described in some detail, many modifications and variations of the preferred embodiment can be made without deviating from the invention. Therefore, it is to be understood that within the scope of the appended claims the invention may be practiced other than as specifically described.

What is claimed is:

1. Apparatus comprising: means for supercritical fluid extraction including,
a breech plug adapted to fit and be fastened sealingly over the open side of an extraction pressure vessel;
first fastening means for fastening the breech plug to the pressure vessel;
mounting means adapted to removably connect a sample holding cartridge to the breech plug;
said breech plug including a wall adapted to receive a latch whereby said breech plug may be fastened and unfastened from the pressure vessel; and
second fastening means for fastening the breech plug permanently to means for moving it from a transport means that positions sample cartridges on it to a pressure vessel, wherein the breech plug may automatically receive sample cartridges and move them into a pressure vessel.

2. Apparatus comprising: means for supercritical fluid extraction including,
pressure vessel means for receiving supercritical fluid;
a sample cartridge sized to fit snugly into the pressure vessel;
a breech plug adapted to have said cartridge mounted to it;
said breech plug including an opening adapted to communicate with an external pressurized fluid and the interior of said sample cartridge;
means for sealingly fastening said breech plug into an opening of said pressure vessel means;
supply means for supplying sample cartridges to said breech plug; and transport means for moving said breech plug between said supply means and said pressure vessel means.

3. Apparatus comprising: means for supercritical fluid extraction of a sample, including:
   a pressure vessel;
   an extraction cartridge having an inlet and an outlet, and a sealing plug;
   means for mounting said cartridge to said sealing plug;
   means for fastening said combination extraction cartridge and sealing plug sealedly into said pressure vessel;
   said pressure vessel having a fluid inlet or outlet which is connected to said inlet of said pressure vessel when said plug is sealedly mounted to said pressure vessel and said extraction cartridge is in said pressure vessel; and
   said pressure vessel having an outlet coupled to said outlet of said extraction cartridge.

4. Apparatus according to claim 3 further including means for preventing contamination from reaching said outlet fitting said means for preventing contamination including means for flushing fluid originating from said inlet across the outside of said extraction cartridge.

5. Apparatus according to claim 3 in which the means for flushing includes means for flushing said fluid through a third port serving as a second outlet in said pressure vessel.

* * * * *